US012558118B2

(12) United States Patent
Gorlewicz et al.

(10) Patent No.: US 12,558,118 B2
(45) Date of Patent: Feb. 24, 2026

(54) SYSTEMS AND METHODS FOR GUIDING SURGICAL TOOLS

(71) Applicants:Saint Louis University, St. Louis, MO (US); Washington University, St. Louis, MO (US)

(72) Inventors: Jenna Gorlewicz, Edwardsville, IL (US); Nnaoma Agwu, Denver, CO (US); Kyle Deprow, East Alton, IL (US); Eric Leuthardt, St. Louis, MO (US)

(73) Assignees: Saint Louis University, St. Louis, MO (US); Washington University, St. Louis, MO (US)

( * ) Notice: Subject to any disclaimer, the term of this patent is extended or adjusted under 35 U.S.C. 154(b) by 0 days.

(21) Appl. No.: 18/756,246

(22) Filed: Jun. 27, 2024

(65) Prior Publication Data

US 2024/0341803 A1     Oct. 17, 2024

Related U.S. Application Data

(62) Division of application No. 17/602,971, filed as application No. PCT/US2020/027625 on Apr. 10, 2020, now Pat. No. 12,048,456.

(60) Provisional application No. 62/831,983, filed on Apr. 10, 2019.

(51) Int. Cl.
*A61B 17/00*     (2006.01)
*A61B 17/34*     (2006.01)

(52) U.S. Cl.
CPC ...... *A61B 17/3403* (2013.01); *A61B 17/3421* (2013.01); *A61B 17/3478* (2013.01); *A61B 2017/00331* (2013.01); *A61B 2017/00991* (2013.01)

(58) Field of Classification Search
CPC .................................................. A61B 17/3403
See application file for complete search history.

(56) References Cited

U.S. PATENT DOCUMENTS

| | | | |
|---|---|---|---|
| 6,086,548 A | 7/2000 | Chaisson et al. |
| 6,471,698 B1 | 10/2002 | Edwards et al. |
| 6,701,173 B2 | 3/2004 | Nowinski et al. |
| 7,883,475 B2 | 2/2011 | Dupont et al. |
| 8,545,515 B2 | 10/2013 | Prisco et al. |
| 9,011,318 B2 | 4/2015 | Choset et al. |
| 9,895,163 B2 | 2/2018 | Trovato |
| 2008/0065106 A1 | 3/2008 | Larkin |
| 2009/0105654 A1 | 4/2009 | Kurth et al. |
| 2010/0114114 A1 | 5/2010 | Tockman et al. |
| 2011/0098678 A1 | 4/2011 | Dupont et al. |
| 2011/0201887 A1 | 8/2011 | Greenblatt et al. |
| 2013/0018303 A1 | 1/2013 | Webster et al. |

(Continued)

OTHER PUBLICATIONS

Pierre E. Dupont, Jesse Lock, Brandon Itkowitz and Evan Butler, Design and Control of Concentric-Tube Robots, IEEE Trans Robot, Apr. 1, 2010; 26(2): 209-225. doi:10.1109/TRO.2009.2035740, 56 pages.

(Continued)

*Primary Examiner* — Joseph M Santos Rodriguez
(74) *Attorney, Agent, or Firm* — Stinson LLP

(57) ABSTRACT

The present disclosure generally relates to systems and methods for guiding surgical tools to a surgical site, and more particularly, to systems and methods for guiding a tool sheath of a delivery system to a surgical site such as a location in a subject's brain and associated surgical procedures.

20 Claims, 17 Drawing Sheets

(56) References Cited

U.S. PATENT DOCUMENTS

| | | |
|---|---|---|
| 2015/0223832 A1 | 8/2015 | Swaney et al. |
| 2017/0119467 A1 | 5/2017 | Leuthardt et al. |

OTHER PUBLICATIONS

Seok Chang Ryu, Zhan Fan Quek, Je-Sung Koh, Pierre Renaud, Richard J. Black, Behzad Moslehi, Bruce L. Daniel, Kyu-Jin Cho, and Mark R. Cutkosky, Design of an[sic] Optically Controlled MR-Compatible Active Needle, IEEE Trans Robot, Feb. 2015; 31(1): 1-11. doi:10.1109/TRO.2014.2367351, 37 pages.

Hunter B. Gilbert, D. Caleb Rucker and Robert J. Webster III, Concentric Tube Robots: The State of the Art and Future Directions, 16 pages.

Robert J. Webster III, Allison M. Okamura, and Noah J. Cowan, Toward Active Cannulas: Miniature Snake-Like Surgical Robots, 7 pages.

L. Frasson, S .Y. Ko, A. Turner, T. Parittotokkaporn, J. F . Vincent and F. Rodriguez Y Baena, Sting: a Soft-tissue Intervention and Neurosurgical Guide to Access Deep brain Lesions Through Curved Trajectories, Jul. 17, 2009; DOI: 10.1243/09544119, 14 pages.

P.E. Dupont, A. Gosline, N. Vasilyev, J. Lock, E. Butler, C. Folk, A. Cohen, R. Chen, G. Schmitz, H. Ren, and P. Del Nido, Concentric Tube Robots for Minimally Invasive Surgery, The Hamlyn Symposium on Medical Robotics (2012), 3 pages.

International Search Report and Written Opinion, PCT/US2020/027625, Jul. 2, 2020, 11 pages.

Ventriculoperitoneal (VP) Shunt

SYSTEMS AND METHODS FOR GUIDING SURGICAL TOOLS

CROSS-REFERENCE TO RELATED APPLICATION

This application is a divisional and claims the benefit of U.S. patent application Ser. No. 17/602,971, filed Oct. 11, 2021, which is the 371 national application of PCT/US2020/027625, filed Apr. 10, 2020, which claims the benefit of U.S. Provisional Patent Application No. 62/831,983, filed Apr. 10, 2019, the entireties of which are hereby incorporated by reference.

FIELD

The present disclosure generally relates to systems and methods for guiding surgical tools to a surgical site, and more particularly, to systems and methods for guiding a tool sheath of a delivery system to a surgical site such as a location in a subject's brain and associated surgical procedures.

BACKGROUND

Currently, deep seated gliomas and brain lesions are treated with using straight trajectory laser ablations through a procedure called Laser Interstitial Thermal Therapy (LITT), which is a minimally invasive treatment option for brain tumors. Neurosurgeons plan out their straight trajectories from MRI scans and use surgical navigation software to position the most efficient way to eliminate the tumor. A 3.2 mm diameter burr hole is created to allow a fiber-optic probe to follow the preset trajectory. A threaded plastic bone anchor is then screwed into the trajectory of the lesion. The fiber-optic probe is then secured to the anchor at the correct depth using navigation software and MRI guidance. Thermal energy by a photo-thermal process from the fiber-optic probe is emitted to ablate the tumor. MRI images are taken to view the effect of the thermography. The ventriculoperitoneal (VP) shunt 1 shown in FIG. 1 is another way for neurosurgeons to access regions of the brain.

There are cases where thermal ablation is not fully effective with damaging the entire tumor. With MRI scans taken, the thermal ablation images will show portions of the tumor unaffected by the ablation. With heat radiating in a spherical or cylindrical shape, tumors often do not resemble these shapes for optimal ablation due to their complex geometries. The use of straight tools and trajectories during LITT limits the ability for the thermal ablation to reach to tumor margins. The neurosurgeon is left with the option to repeat the ablation application to the tumor with another burr hole to access the desired region. This increases the time of the operation and risk of infection and complications. Healthy brain tissue is also at risk if multiple trajectories are created for ablations.

Although there is extensive work in needle-based neurosurgery, many of these systems are also limited to using straight trajectories under image guidance. There is a body of research on steerable medical devices, including needles and continuum robots such as active cannulas. Both steerable needles and active cannulas have small form factors, are biocompatible, and offer methods for reaching targets along a curved path. Active cannulas 2 (FIG. 2) provide dexterous motion due to their elastic, precurved concentric telescoping tubes. The active cannula 2 is typically comprised of multiple, concentric, needle-like tubes, at least one of which is precurved and superelastic, whose properties are selected a priori based on task requirements. These designs often lead to intricate, complex configurations, sometimes consisting of three or more tubes. The active cannula 2 shown in FIG. 2 displays a concentric tube design, which of four superelastic Nitinol tubes that can rotate and translate with respect to one another. Alternate approaches also exist such as a two tube design, where additional tubes could be added or removed during surgery for hemorrhage evacuation. There remains a need for new systems and methods to access surgical sites, particularly surgical sites within the brain, that are not limited to straight trajectories.

SUMMARY

Various aspects of the present disclosure relate to methods for accessing a surgical site in a subject. In some embodiments, these methods comprise advancing a distal end of a delivery system through body tissue of the subject to position the distal end of the delivery system in the body tissue and a proximal end of the delivery system outside the body tissue. The delivery system is configured to guide a surgical tool to the surgical site. The delivery system includes a delivery sleeve having a longitudinal axis extending between proximal and distal ends of the delivery system, a tool sheath movably disposed longitudinally within the delivery sleeve, and a first guide movably disposed longitudinally within the tool sheath. The methods include guiding the distal end of the delivery system to the surgical site by longitudinally moving the first guide and the tool sheath relative to the delivery sleeve. The methods include retracting the first guide proximally through the tool sheath such that the distal end of the delivery system is defined by the distal end of the tool sheath.

Other aspects of the disclosure relate to methods of performing a surgical procedure in a subject's brain. In various embodiments, these methods comprise accessing the surgical site within the subject's brain according to a method as described herein. The methods also include advancing a surgical tool distally though the tool sheath to position the surgical tool at the surgical site and operating the surgical tool.

Further aspects of the disclosure relate to delivery systems for guiding a surgical tool to a surgical site. In various embodiments, the delivery systems comprise a delivery sleeve having a longitudinal axis and proximal and distal ends spaced apart from one another along the longitudinal axis. The delivery sleeve is configured to be inserted into the body tissue of a subject. A tool sheath is movably disposed longitudinally within the delivery sleeve. The tool sheath defines a lumen configured to receive the surgical tool. A first guide is movably disposed longitudinally in the lumen of the tool sheath. The first guide is deformable and has a generally curved shape when the first guide is not deformed. The first guide and tool sheath are configured to be moved distal of the delivery sleeve so that the first guide can guide a distal end of the tool sheath to the surgical site. The first guide is deformed when the first guide is disposed within the delivery sleeve and at least a portion of the first guide has a generally curved shape when the first guide is moved distally through the distal end of the delivery sleeve. The tool sheath is flexible and generally conforms to the shape of the first guide.

Further aspects of the disclosure relate to delivery systems for guiding a surgical tool to a surgical site. In various embodiments, the delivery systems comprise a first guide having a longitudinal axis and proximal and distal ends spaced apart from one another along the longitudinal axis. The first guide is configured to be inserted into the body tissue of a subject. The first guide defines a lumen extending between the proximal and distal ends. The first guide is deformable and has a generally curved shape when the first guide is not deformed. A second guide is movably disposed in the lumen of the first guide. The second guide is deformable and has a generally curved shape when the second guide is not deformed. The longitudinal axis has a first shape when the first and second guides are disposed relative to one another in a first configuration and a second shape different than the first shape when the first and second guides are disposed relative to one another in a second configuration.

Other objects and features will be in part apparent and in part pointed out hereinafter.

BRIEF DESCRIPTION OF THE SEVERAL VIEWS OF THE DRAWINGS

Corresponding reference characters indicate corresponding parts throughout the drawings.

DETAILED DESCRIPTION

Figure 1:
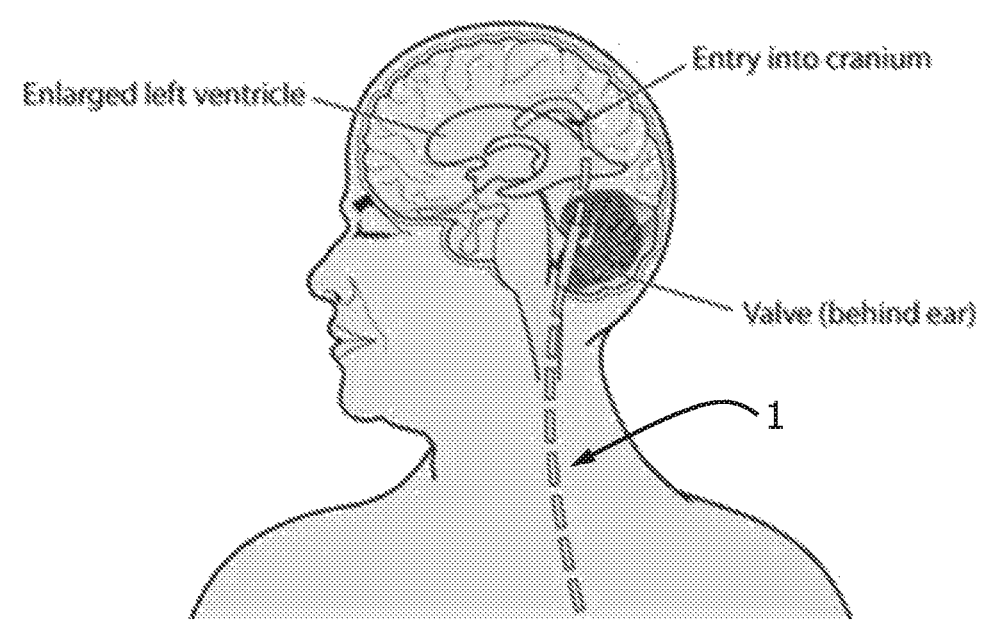
FIG. 1 is an illustration of complex ventricle targeting for shunt placement.
Figure 2:
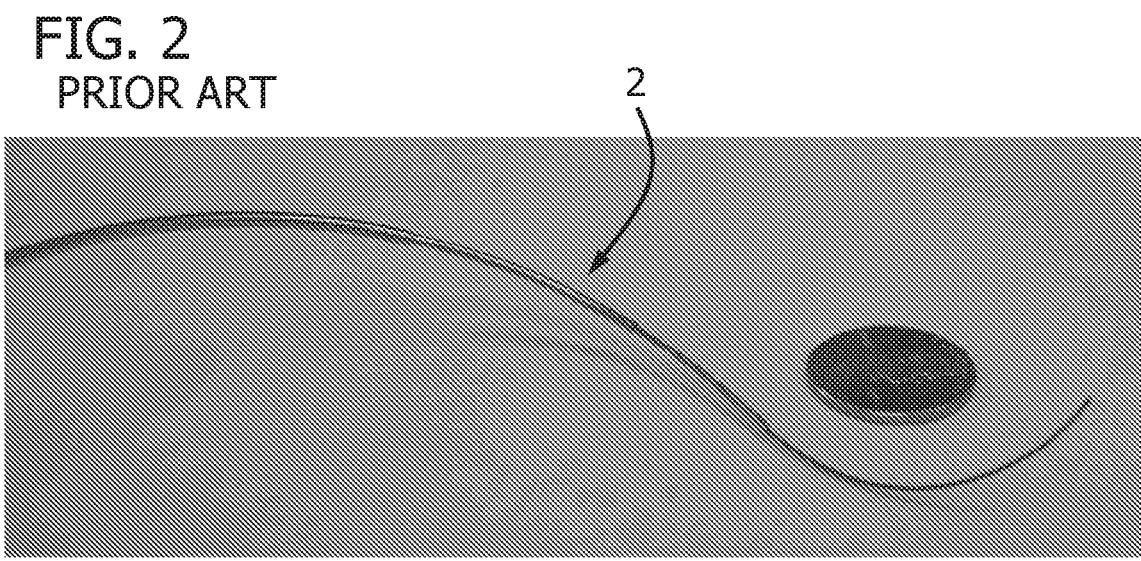
FIG. 2 is an image of an active cannula system with minimally invasive concentric tubes.
Figure 3:
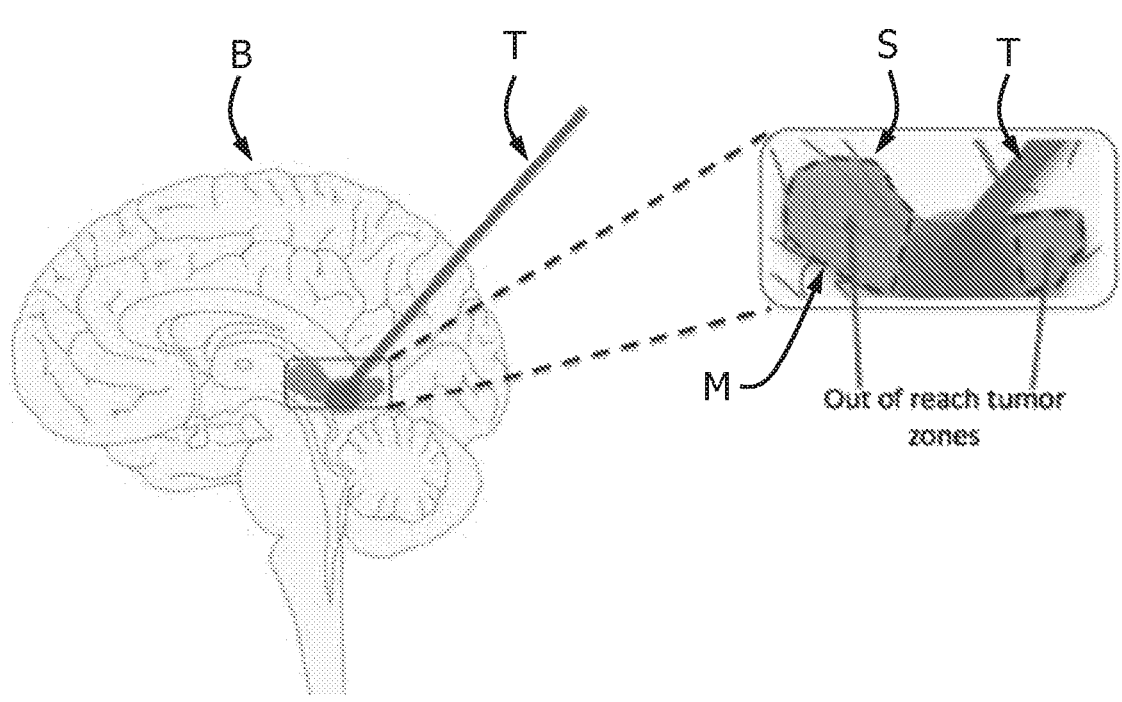
FIG. 3 is an illustration of inaccessible regions of surgical site of a subject's brain using straight trajectory laser ablations.

In general, the systems and methods described herein are for guiding or steering existing straight, but flexible surgical tools T to a surgical site S. The surgical site S may be located within any portion of the subject's body, such as the brain B (FIG. 3). The delivery systems (e.g., curved port delivery system, port delivery system, cannula delivery system) as described herein enables surgical tools T that aren't inherently steerable, to be able to be steered to desired off-axis targets. Moreover, the delivery systems are biocompatible/MRI-compatible and retains surgical workflow of existing procedures, while adding enhanced dexterity when needed.

Moreover, the delivery systems enable existing imaging technologies to image the surgical tool T and the surgical site S without interfering with the image. It has been observed that existing cannula systems using Nitinol tubes interfere with thermometry readings when the Nitinol is too proximate to the laser tip (e.g., surgical tool). For example, Nitinol in these existing cannula systems causes imaging artifacts (e.g., distortions) during MRI's and thermometry artifacts during LITT. Nitinol is a nickel-titanium alloy. Existing cannula systems using Nitinol tubes to guide the laser tip to the surgical site are not sufficiently thermometry compatible for accurate tip (e.g., probe) placement because of the heat generated during LITT. As explained in more detail below, because the delivery system described herein may use components containing Nitinol to guide a tool sheath to the surgical site, but then be subsequently removed from the surgical site S after the placement of a tool sheath, the delivery system is able to guide a surgical tool T to a surgical site without interfering or distorting images taken of the surgical site and tool thereat. Such a delivery system can be used in neurosurgical applications where imaging accuracy and in the case of tumor ablation, thermometry accuracy, are paramount, such as LITT.

Figure 19:
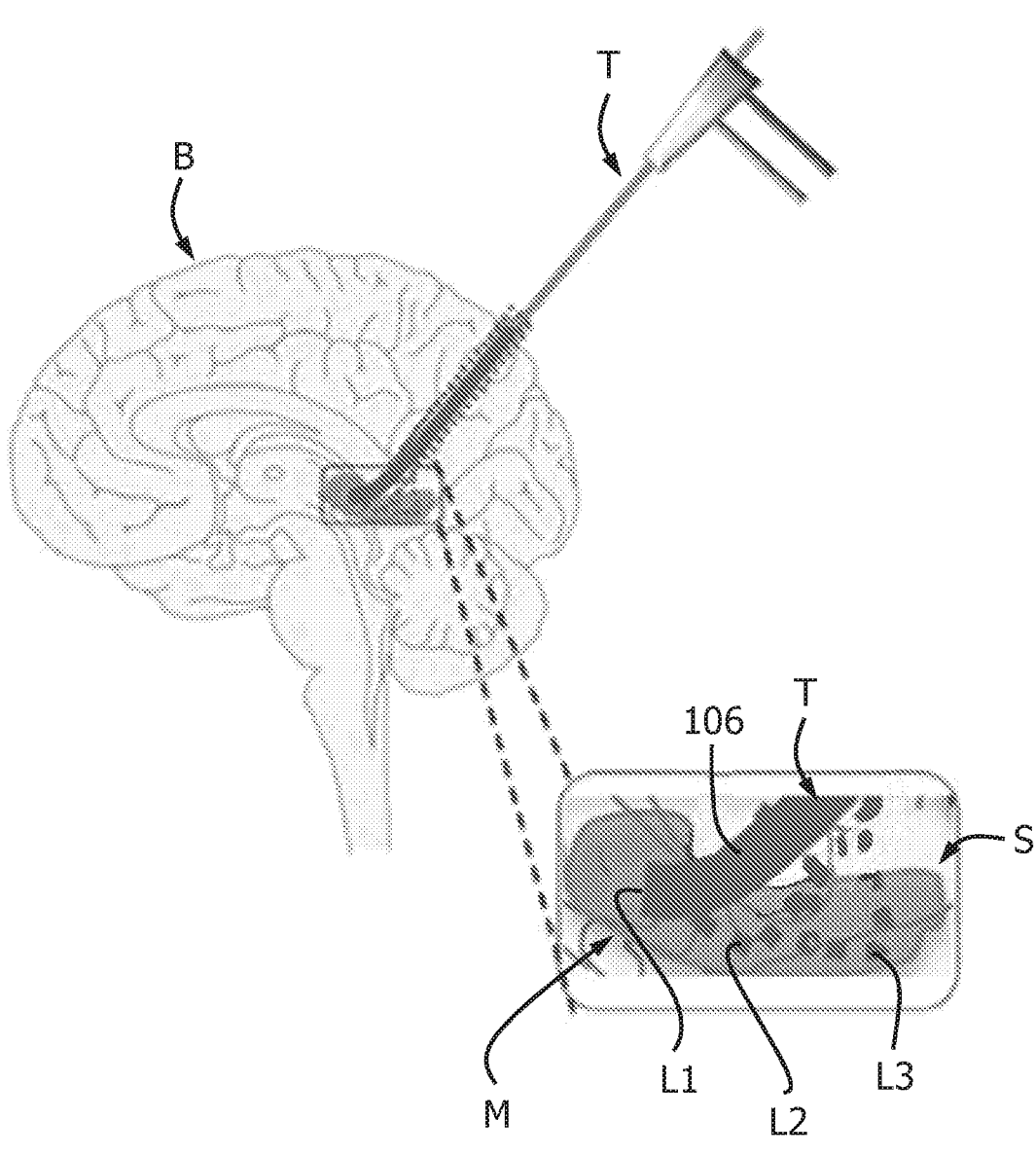
FIG. 19 is an illustration of the delivery system guiding a surgical tool to a surgical site.

Considering that many neurosurgical laser ablation catheters and surgical probes (which are types of surgical tools T) are already inherently flexible, MRI-compatible, biocompatible, and thermometry-compatible, the end objective primarily sits in their ability to be steered to a targeted location. As opposed to significantly modifying these existing tools (or designing entirely new ones) to be steerable, the delivery system enables these flexible surgical instruments T to be steered or guided to desired locations (e.g., surgical site S). In other words, the delivery systems provide steerability to surgical tools T that are otherwise not steerable. This allows the surgical procedure, such as LITT, to be conducted by starting with a straight, flexible surgical tool T, as it normally done. When the surgeon reaches a point during the procedure where more dexterity is needed, one of the delivery systems according to the present disclosure is used. The delivery systems enable the surgeon to deploy a biocompatible, MRI-compatible, and thermometry-compatible plastic port (broadly, a tool sheath) along a desired curved trajectory to the surgical site S. This port serves as a guide to "steer" the existing flexible tools T used in the surgical procedure to new targets that were otherwise unreachable using the straight surgical tool (FIGS. 3 and 19). The delivery systems allow existing surgical tools T to be operated normally but now along a curved trajectory. Once the targeted locations S have been reached, the surgical tools T are removed from the port, and the port is retracted out via the same deployment system. The procedure then continues as it normally would. Using the delivery systems, as described herein, provide several advantages such as (1) the surgical tools T themselves would not be significantly altered and would maintain current standards of functionality, clearance, and compatibility; (2) the system supports a number of different surgical tools within a given size restriction, making it a more universal solution; (3) the surgical workflow would largely remain consistent; and (4) enhanced dexterity and capability is still provided to the surgeon for treatment, affording the potential for better patient outcomes.

The delivery systems as disclosed herein may act as part of a touch up tool to ablate complex geometrically shaped tumors M that otherwise would not be ablated with a normal straight trajectory surgical tools T (FIG. 3), such as a fiber-optic probe or laser ablations. After thermal ablation is applied to the tumor M, neurosurgeons can use MRI to evaluate how effective the surgical tool T (e.g., fiber-optic probe) was. If it is determined that significant portions of the tumor M remain at the surgical site S, the delivery system can deliver a port or tool sheath into unique locations using the single burr hole used in the LITT procedure (FIG. 19). Upon the placement of the curved port or tool sheath in the brain B, the fiber-optic probe T follows the created path of the port or tool sheath. This enables neurosurgeons to reach unique locations of the tumor M outside the range of the straight trajectories first used (FIGS. 3 and 19). With the ability to reach more areas, lower heating profiles can be used decreasing the risk of harming healthy brain B tissue.

Typically, the tool sheath (as described in more detail below) is constructed of a polymer. In various embodiments, the polymer comprises a polyamide, such as a synthetic polyamide (e.g., various nylons including nylon 6,6 and nylon 6), polyvinyl chloride (PVC), polycaprolactone (PCL), polydioxanone (PDO), or a fluoropolymer. Fluoropolymers include, for example, polytetrafluoroethylene (PTFE), fluorinated ethylene-propylene (FEP), perfluoro-alkoxy resin (PFE, a copolymer of tetrafluoroethylene and perfluorovinylethers), ethylene-tetrafluoroethylene copolymer (ETFE), polychlorotrifluoroethylene (PCTFE), ethylene-chloro-trifluoroethylene copolymer (ECTFE), polyvinylidene fluoride (PVDF), and polyvinyl fluoride (PVF). Preferably the fluoropolymer is PTFE.

Having explained some of the general features of the present disclosure, more detailed embodiments of the delivery system will now be described.

Referring to FIGS. 4-18, one embodiment of a delivery system for guiding a surgical tool T to a surgical site within the body tissue is generally indicated by reference numeral 100. The delivery system 100 may include an elongate body or delivery sleeve 102 (FIG. 10) having a longitudinal axis LA and proximal and distal ends spaced apart from one another along the longitudinal axis. The delivery sleeve 102 is configured to be inserted into the body tissue (e.g., brain B) of a subject. The delivery sleeve is generally straight and rigid. The delivery sleeve 102 defines a delivery sleeve lumen 104 extending along the longitudinal axis LA between the proximal and distal ends. The delivery system 100 also includes a tool sheath 106 (as described above) movably disposed longitudinally within the delivery sleeve 102 (e.g., the lumen 104 thereof). For reasons that will become apparent, the length of the delivery sleeve 102 is less than the length of the tool sheath 106. The tool sheath 106 defines a tool sheath lumen 108 configured to receive the surgical tool S. The tool sheath lumen 108 extends between proximal and distal ends 109, 111 of the tool sheath 106.

Figure 13:
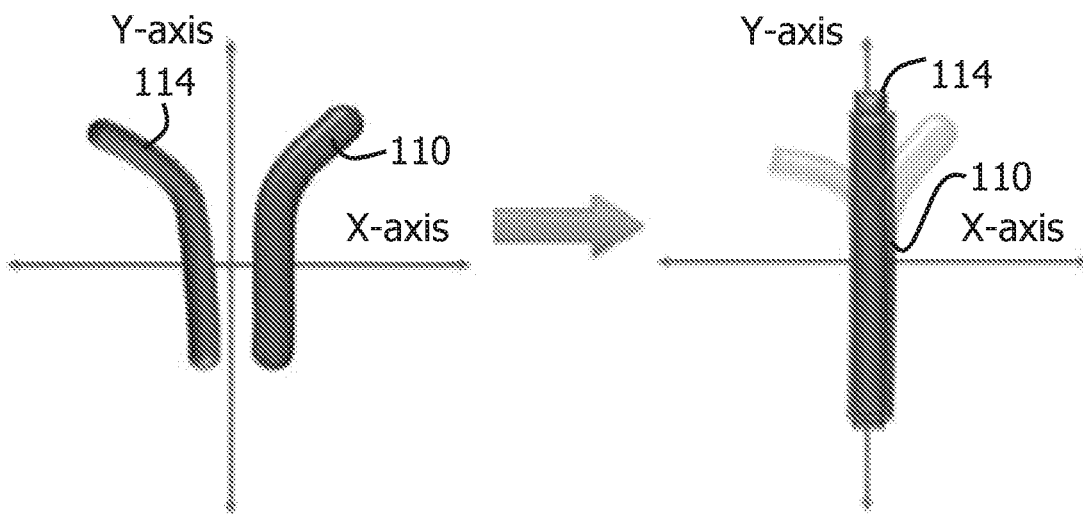
FIG. 13 is an illustration of the first and second guides in a first configuration to create a straight trajectory.
Figure 14:
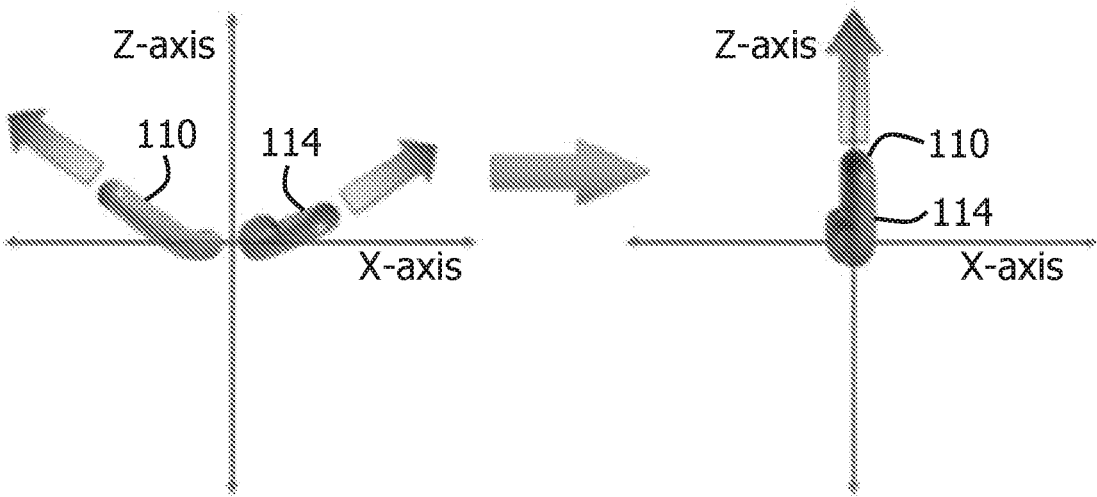
FIG. 14 is an illustration of the first and second guides in a second configuration to create a curved trajectory.
Figure 15:
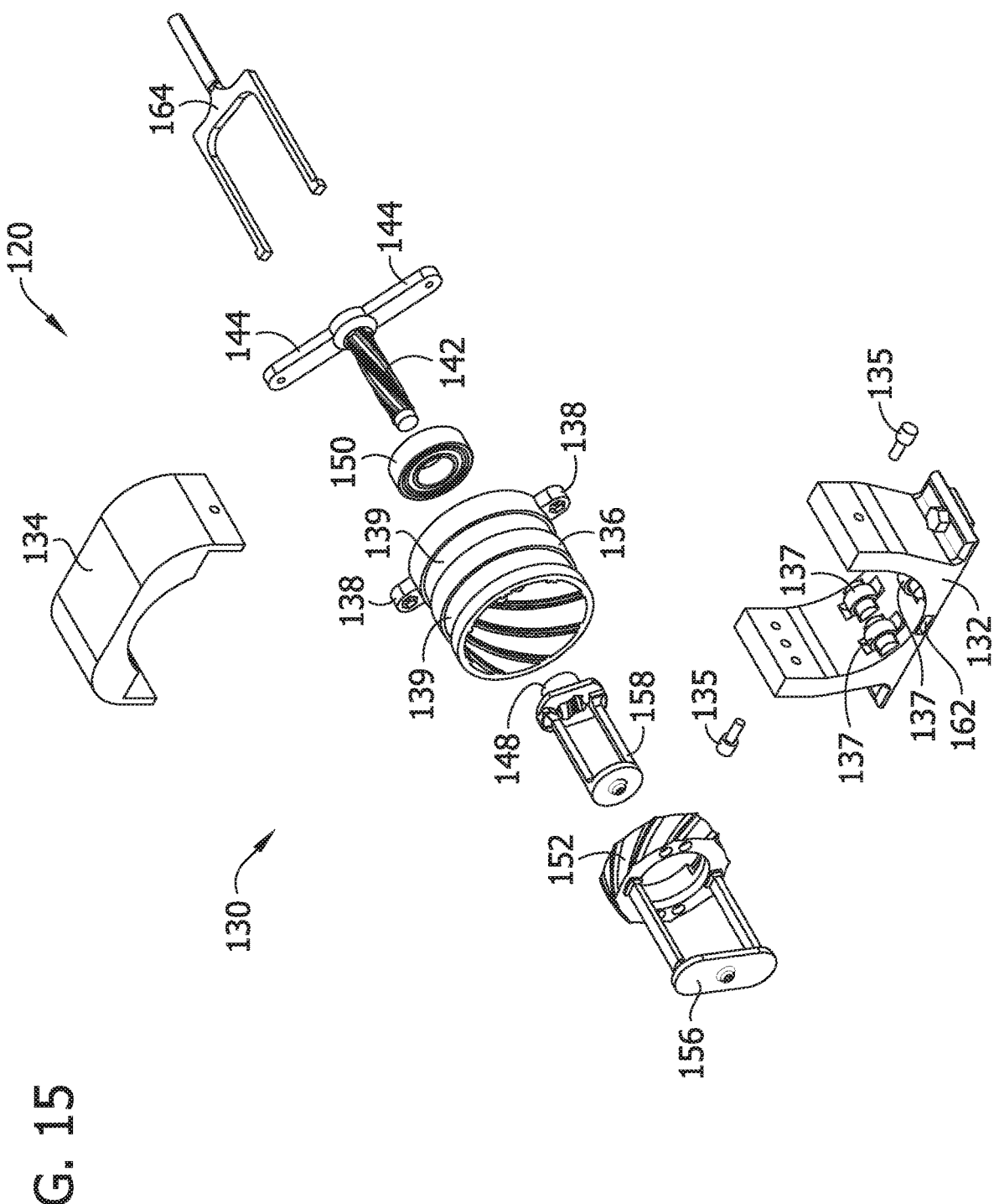
FIG. 15 is an exploded view of the drive assembly.

The delivery system 100 also includes a first guide 110 (e.g., a first tube) movably disposed in the lumen 108 of the tool sheath 106. The first guide 110 may move longitudinally and/or rotationally within the tool sheath 106. The first guide 110 may define a first guide lumen 112 extending between the proximal and distal ends of the first guide. The first guide lumen 112 may extend between proximal and distal ends of the first guide 110. The first guide 110 is deformable and has a generally curved shape when the first guide is not deformed (FIGS. 13 and 14). Preferably, a distal portion of the first guide 110 is curved when the first guide is unrestricted (e.g., not deformed). In one embodiment, the distal portion is about the distal third of the length of the first guide 110. The first guide 110 and tool sheath 106 are configured to be moved distal of the delivery sleeve 102 so that the first guide can guide the distal end 109 of the tool sheath 106 to the surgical site S (e.g., a particular location within the surgical site). The first guide 110 is deformed when the first guide is disposed within the delivery sleeve 102 (because the delivery sleeve is generally rigid). In particular, the first guide 110 is generally straight when disposed within the delivery sleeve 102. At least a portion of the first guide 110 (e.g., the portion of the first guide distal of the delivery sleeve 102) has a generally curved shape when the first guide is moved (e.g., advanced) distally through the distal end of the delivery sleeve. This is because the portion of the first guide 110 outside of the delivery sleeve 102 is no longer constrained (e.g., deforming) by the delivery sleeve, permitting the portion of the first guide outside the delivery sleeve to return to its nature, curved state. The tool sheath 106 is flexible and generally conforms to the shape of the first guide 110. Thus, the portion of the tool sheath 106 disposed outside the delivery sleeve 102 that houses the portion of the first guide 110 which is curved (because it is also outside the delivery sleeve), also becomes curved.

The delivery system 100 may also include a second guide 114 (e.g., a second tube) movably disposed longitudinally within the first guide 110 (e.g., the lumen 112 thereof). The second guide 114 operates in the same manner as the first guide 110. The second guide 114 is deformable and has a generally curved shape when the second guide is not deformed. The second guide 114 may have the same or different curve as the first guide 110. Preferably, a distal portion of the second guide 114 is curved when the second guide is unrestricted (e.g., not deformed). In one embodiment, the distal portion is about the distal third of the length of the second guide 114. The second guide 114 is deformed when the second guide is disposed within the delivery sleeve 102. Other ways of deforming the first and second guides 110, 114 are within the scope of the present disclosure. For example, the first and second guides 110, 114 can deform each other as discussed in more detail below. The first and second guides 110, 114 and tool sheath 106 are configured to be moved distal of the distal end of the delivery sleeve 102 so that the first and second guides can guide the distal end 109 of the tool sheath to the surgical site S. The first and/or second guides 110, 114 serve as the steering backbone of the tool sheath 106 (broadly, the delivery system 100) and create the non-sweeping, curved trajectories that guide the distal end of the delivery system (e.g., the distal end 109 of the tool sheath) to a desired location within the surgical site S of the subject's brain B. In this embodiment, the delivery system 100 may not include the delivery sleeve 102 because the interaction between the first and second guides 110, 114 is able to straighten and curve the longitudinal axis LA, as discussed in more detail below. The first and second guides 110, 114 are generally aligned with (e.g., define) the longitudinal axis LA.

The first and second guides 110, 114 are configured to move at least one of longitudinally and rotationally relative to one another to change the relative shapes of the first and second guides (e.g., the longitudinal axis LA). In this manner, by selectively positioning, longitudinally and rotationally, the first and second guides 110, 114 relative to one another, the particular shape defined by the first and second guides can change to guide the tool sheath 106 to different locations at the surgical site S. In other words, because both the first and second guides 110, 114 are elastic and curved in an undeformed state, positioning the first and second guides relative to one another changes the curved trajectory or path (e.g., the longitudinal axis LA) defined by the combination of or interaction between the first and second guides. Specifically, the longitudinal axis LA has a first shape (e.g., straight) when the first and second guides 110, 114 are disposed relative to one another in a first configuration (FIGS. 4, 5 and 13) and a second shape (e.g., curved) different than the first shape when the first and second guides are disposed relative to one another in a second configuration (FIGS. 6-8 and 14). In one embodiment, as shown in FIG. 13, positioning the first and second guides 110, 114 in the first configuration such that the guides are 180 degrees relative to one another (such the curves are curving in opposite directions) results in the first and second guides (e.g., the longitudinal axis LA) having a generally straight shape (e.g., the elastic forces of the guides generally offset one another). Similarly, as shown in FIG. 14, positioning the first and second guides 110, 114 relative to one another in a second configuration (different than the first) results in the first and second guides having a generally curved shape—the degree of the curve becoming larger as the first and second guides are rotated into alignment with the maximum degree of curvature occurring with the curves of the first and second guides are aligned. It is understood the second configuration of the first and second guides 110, 114 may be generally any position of the first and second guides relative to one another to get any desired degree of curvature between 0 (e.g., straight) and the maximum degree of curvature (including the maximum degree of curvature). Thus, as will become apparent, a surgeon can rotate the first and second guides 110, 114 relative to one another to create the necessary trajectory to reach other locations of the surgical site S (e.g., locations out of reach of a straight line). When the delivery system 100 includes the second guide 114, the tool sheath 106 generally conforms to the shapes of the first and second guides (e.g., conforms to the path or longitudinal axis LA defined by the first and second guides and the interactions thereof).

In this embodiment, the first guide 110 (and second guide 114 when included) of the delivery system 100 is configured to be removed from the lumen 108 of the tool sheath 106 to permit the surgical tool T to be inserted into the lumen. Thus, once the first and/or second guides 110, 114 have positioned the tool sheath 106 at the surgical site S, the first and/or second guides are removed. In one embodiment, the first and second guides 110, 114 comprise (e.g., are made of) a nickel-titanium shape memory allow such as Nitinol. As mentioned above, Nitinol can interfere with imaging of the surgical site S. But by removing the first and second guides 110, 114 from the tool sheath 106 once the tool sheath has been positioned at the desired location at the surgical site S, no components of the delivery system 100 containing Nitinol are positioned at the surgical site when the surgical tool is at the surgical site—allowing clear images to be generated of the surgical tool at the surgical site. Accordingly, the tool sheath 106 is preferably free of Nitinol or other materials that would interfere with imaging the surgical site S. In some embodiments, the first and second guides 110, 114 may also comprise (e.g., be constructed of) other materials such as one or more polymers. For example, such polymers include polyamides, such as synthetic polyamides (e.g., various nylons including nylon 6,6 and nylon 6), polyvinyl chloride (PVC), polycaprolactone (PCL), polydioxanone (PDO), or a fluoropolymer. Fluoropolymers include, for example, poly-tetrafluoroethylene (PTFE), fluorinated ethylene-propylene (FEP), perfluoroalkoxy resin (PFE, a copolymer of tetrafluoroethylene and perfluorovinylethers), ethylene-tetrafluoroethylene copolymer (ETFE), polychlorotrifluoroethylene (PCTFE), ethylene-chloro-trifluoroethylene copolymer (ECTFE), polyvinylidene fluoride (PVDF), and polyvinyl fluoride (PVF). Preferably the fluoropolymer is PTFE. Such biocompatible polymers do not interfere with the imaging of the surgical site S, permitting the first and second guides 110, 114 to remain at the surgical site as described in more detail below.

The delivery system 100 leverages the first and/or second guides 110, 114 to guide the distal end of the delivery system to the surgical site S. In one embodiment, the first and second guides 110, 114 are needle-sized, tentacle-like tubes. As mentioned above, in one embodiment, these tubes 110, 114 are pre-curved, superelastic Nitinol, enabling them to telescope in and out of one another and rotate axially with respect to one another. These types of Nitinol tubes 110, 114 are well-suited for neurosurgical applications, with advantages including (1) the ability to traverse along straight or curved paths in a follow-the-leader style—meaning they can be deployed and retracted along the same path and cause little to no "sweeping" of tissue, (2) they have a small size (e.g., form factor), with some as small as 0.5 mm in outer diameter, and (3) they are biocompatible and are limited MRI-compatible.

As mentioned above, the disadvantage to the existing systems that use Nitinol is that Nitinol is not well-suited for thermometry, and while MRI-compatible up to a certain point, still leaves some artifacts in imaging. However, plastic materials do not possess such disadvantages. However, most plastics do not possess the inherent superelastic nature of Nitinol, which is why Nitinol is particularly well suited for generating paths for surgical tools T. The delivery systems 100 of the present disclosure provide the advantages of each of these components, using the Nitinol-based guides 110, 114 for delivery of a plastic tool sheath 106, which then becomes the primary channel for deploying surgical tools T once the guides are retracted (leaving the tool sheath as the only component of the delivery system at the surgical site). This approach leverages the advantages of both systems to provide steerability to the surgical site S via the guides 110, 114 and imaging characteristics of the plastic tool sheath 106.

The delivery system 100 generally uses a three tube design: (1) a straight outer delivery sleeve 102; (2) first and/or second guides 110, 114; and (3) the plastic tool sheath 106. In one embodiment, the first guide 110 has an outer diameter of about 2.311 mm and an inner (e.g., lumen 112) diameter of about 2.108 mm, the second guide 114 has an outer diameter of about 1.854 mm and an inner (e.g., lumen) diameter of about 1.702 mm, and the tool sheath 106 has an outer diameter of about 3.97 mm and an inner (e.g., lumen 108) diameter of about 2.38 mm. This delivery system 100 provides sufficient dexterity needed for retraction and deployment without the complexity that comes with a larger number of tubes. The straight outer delivery sleeve 102 provides a translational degree of freedom that enables easy control of the depth at which curved trajectory begins. In operation, the tool sheath 106, the first guide 110 and the second guide 114 extend through the delivery sleeve 102 to reach the surgical site S. The delivery system 100 can be mounted onto an existing clinical setup and would be positioned using a linear slide or track, as described in more detail below. The first and second guides 110 are pre-curved and placed concentrically inside the straight outer delivery sleeve 102, enabling curved trajectories to be achieved upon deployment from the delivery sleeve. The first and second guides 110, 114 may achieve various different curved trajectories by the interaction of forces from their pre-curvatures. As shown in FIGS. 13 and 14, the two guides 110, 114 can achieve straight and curved trajectories by translating and rotating the two guides in and out of phase with one another.

The delivery system 100 may also include a drive assembly, generally indicated at 120, configured to be engaged by a surgeon or operator to control the operation of the delivery system. The drive assembly 120 is operatively connected to the delivery sleeve 102, the tool sheath 106 and the first guide 110 and is configured to move the delivery sleeve, the tool sheath and the first guide into the body tissue of the subject. The drive assembly 120 is configured to move the delivery sleeve 102, the tool sheath 106 and the first guide 110 together into the body tissue of the subject. In addition, the drive assembly 120 is configured to move each of the delivery sleeve 102, the tool sheath 106 and the first guide 110 relative to one another. For example, the drive assembly 120 is configured to move the tool sheath 106 relative to the delivery sleeve 102. The drive assembly 120 is also configured to rotate the first guide 110 relative to the delivery sleeve 102 and the tool sheath 106. If included, the drive assembly 120 is also configured to rotate the second guide 114 relative to the delivery sleeve 102, the tool sheath 106 and the first guide 110.

In one embodiment, the drive assembly 120 may permit the surgeon to individually control the longitudinal and/or rotational position of the delivery sleeve 102, the tool sheath 106, the first guide 110 and the second guide 114. The drive system 120 may include individual actuators operatively connected to each of the delivery sleeve 102, the tool sheath 106, the first guide 110 and second guide 114 to control the movement (e.g., longitudinal and/or rotational) thereof. For example, the actuator operatively connected to the delivery sleeve 102 can be used to move the delivery sleeve proximally and distally along the longitudinal axis LA. The actuator operatively connected to the tool sheath 106 can be used to move the tool sheath proximally and distally relative to the delivery sleeve 102 and along the longitudinal axis LA. The actuator operatively connected to the first guide 110 can be used to move the first guide proximally and distally relative to the delivery sleeve 102 and/or the tool sheath 106 (e.g., the longitudinal axis LA) and/or rotate the first guide relative to the delivery sleeve and/or the tool sheath. The actuator operatively connected to the second guide 114 can be used to move the second guide proximally and distally relative to the delivery sleeve 102, the tool sheath 106 and/or the first guide 110 (e.g., the longitudinal axis LA) and/or rotate the second guide relative to the delivery sleeve, the tool sheath and/or first guide. Other configurations of the drive assembly 120 are within the scope of the present disclosure. For example, two or more of the actuators may be longitudinally and/or rotatably coupled together such that the two or more actuators move together (e.g., simultaneously). For example, the actuators of the tool sheath 106, the first guide 110 and the second guide 114 may be longitudinally coupled together such that these components move together along the longitudinal axis LA. Moreover, the two or more actuators may be releasable coupled together, such that when connected the two or more actuators move together and when disconnected, the two or more actuators move independently.

In one embodiment, a single actuator is operatively connected to both the first and second guides 110, 114 to move the first and second guides relative to one another, the delivery sleeve 102 and/or the tool sheath 106. In this embodiment, the single actuator may also be operatively connected to the both the first and second guides 110, 114 to rotate the first and second guide relative to one another, the delivery sleeve 102 and/or the tool sheath 106. For example, the single actuator may be operatively connected to the first and second guides 110, 114 such that movement of the single actuator rotates the first guide in one direction (e.g., clockwise) and the second guide in the opposite direction (e.g., counter-clockwise) at the same time. All the actuators may be mounted on a track that allows each actuator (collectively or individually) to move along the track. The actuators may also be selectively lockable in position on the track.

Referring to FIGS. 4-9 and 15-18, one embodiment of the drive assembly 120 is generally shown. In this embodiment, the drive assembly 120 enables the translation of the tool sheath 106, the first guide 110 and the second guide 114 along the longitudinal axis LA and the rotations of the first and second guides about the longitudinal axis to occur simultaneously and through the use of a single actuator. The drive assembly 120 includes a rail or track 122 on which the delivery sleeve 102, the tool sheath 106 and the first and second guides 110, 114 are movably mounted. The track 122 allows the delivery sleeve 102, the tool sheath 106 and the first and second guides 110, 114 to move along the longitudinal axis LA to control the overall depth of the delivery system 100 in the tissue of the subject. The track 122 is generally parallel to the longitudinal axis LA. The drive assembly 120 includes a tool sheath mount 124. The tool sheath mount 124 is slidably mounted on the track 122 and may include a first retainer 126 (e.g., a fastener) used to secure the tool sheath mount in position on the track. The tool sheath mount 124 is coupled to and supports the tool sheath 106. The tool sheath mount 124 may include a tool sheath retainer 128 (e.g., a set screw) used to releasably couple the tool sheath 106 to the tool sheath mount 124. The drive assembly 120 may also include a delivery sleeve mount (not shown), which is generally identical to the tool sheath mount 124. The delivery sleeve mount is mounted distally of the tool sheath mount 124 on the track 122.

The drive assembly 120 includes a guide mount 130 coupled to and supporting the first and second guides 110, 114. The guide mount 130 is proximal of the tool sheath mount 124. The guide mount 130 permits the longitudinal and rotational movement of the first and second guides 110, 114. The guide mount 130 is slidably mounted on the track 122. The guide mount 130 includes a lower housing 132 and an upper housing 134 coupled together. The lower and upper housings 134 may be releasably secured together by fasteners 135 (e.g., bolts, set screws, etc.). The lower and upper housings 132, 134 define an opening extending therethrough. The opening is generally aligned with the longitudinal axis LA. Disposed within opening is a guide collar 136. The guide collar 136 is internally threaded for reasons that will become apparent. The guide collar 136 is generally aligned with the longitudinal axis LA. As explained in more detail below, the guide collar 136 guides the longitudinal and rotational movement of the first guide 110 relative to the longitudinal axis LA. The guide collar 136 is rotatably disposed within the lower and upper housings 132, 134 (e.g., the guide collar 136 can rotate about the longitudinal axis LA). One or more bearings 137 rotatably support the guide collar 136. In the illustrated embodiment, four bearings 137 are used. The guide collar 136 may include one or more exterior circumferential grooves 139 which receive the bearings 137. The guide collar 136 includes first and second locking tabs 138 used to lock or secure the position of the guide collar relative to the lower and upper housings 132, 134. In this embodiment, each locking tab 138 includes an opening that aligns with one of the openings 140 on the back of the lower and upper housings 132, 134 (FIG. 7) so that a retainer (not shown), such as a fastener, can extend therein to secure the position of the guide collar 136 relative to the lower and upper housings. Changing the position of the guide collar 136 relative to the lower and upper housings 132, 134 (via the openings 140) changes the direction of curvature (e.g., the direction of the curved trajectory) that results when the first and second guides 110, 114 rotate and/or translate relative to one another.

The drive assembly 120 also includes a guide shaft 142 disposed within the guide collar 136. The guide shaft 142 is externally threaded for reasons that will become apparent. The threads of the guide shaft 142 rotate in generally the opposite direction as the threads of the guide collar 136. As explained in more detail below, the guide shaft 142 guides the longitudinal and rotational movement of the second guide 114 relative to the longitudinal axis LA. The guide shaft 142 is generally aligned with the longitudinal axis LA. The guide shaft 142 is rotatably disposed within the guide collar 136 (e.g., the guide shaft 142 can rotate about the longitudinal axis LA). In this embodiment, the guide shaft 142 includes first and second locking tabs 144 used to support and secure the position of the guide shaft relative to the lower and upper housings 132, 134 and the guide collar 136. In this embodiment, each locking tab 144 includes an opening that aligns with one of the openings 140 on the back of the lower and upper housings 132, 134 (FIG. 7) so that a retainer (not shown), such as a fastener, can extend therein to secure the position of the guide shaft 142 relative to the lower and upper housings. Preferably, the same retainers may be used to secure the guide collar 136 and guide shaft 142 relative to the lower and upper housings 134. Changing the position of the guide shaft 142 relative to the lower and upper housings 132, 134 (via the openings) changes the direction of curvature (e.g., the direction of the curved trajectory) that results when the first and second guides 110, 114 rotate and/or translate relative to one another. In the illustrated embodiment, the guide collar 136 and guide shaft 142 are positioned relative to the lower and upper housings 132, 134 such that the curved trajectory is generally downward as shown in FIG. 8. However, if the guide collar 136 and guide shaft 142 are rotated 180 degrees relative to the lower and upper housings 132, 134, the direction of the curved trajectory would be generally upward (not shown). Preferably, the guide collar 136 and guide shaft 142 are rotated relative to the lower and upper housings 132, 134 together.

The drive assembly 120 includes a rotation drive assembly 146 (FIGS. 16 and 17) disposed between the guide shaft 142 and the guide collar 136. The rotation drive assembly 146 permits the first and second guides 110, 114 to rotate relative to one another. The rotation drive assembly 146 also moves the first and second guides 110, 114 together longitudinally along the longitudinal axis LA. The rotation drive assembly 146 includes an inner collar 148, a bearing 150 and an outer collar 152. The inner collar 148, the bearing 150 and the outer collar 152 are all aligned with the longitudinal axis LA. The inner collar 148 is mount to the inner circumferential surface of the bearing 150 and the outer collar 152 is mounted to the outer circumferential surface of the bearing. The bearing 150 permits the inner and outer collars 148, 152 to rotate relative to one another. The inner collar 148 is internally threaded and engages the external threads of the guide shaft 142. The outer collar 152 is externally threaded and engages the internal threads of the guide collar 136. As explained in more detail below, the engagement between the threads of the inner collar 148 and the guide shaft 142 rotates the inner collar in a first direction about the longitudinal axis LA and the engagement between the threads of the outer collar 152 and the guide collar 136 rotates the outer collar in a second direction (opposite the first direction) about the longitudinal axis when the rotation drive assembly 146 moves longitudinally along the longitudinal axis. The rotation drive assembly 146 includes a first carriage 156 mounted to the outer collar 152. The first carriage 156 couples to the first guide 110. Accordingly, rotation of the outer collar 152 rotates the first carriage 156 which rotates the first guide 110. Likewise, translation of the outer collar 152 translates the first carriage 156 which translates the first guide 110 along the longitudinal axis LA. The rotation drive assembly 146 includes a second carriage 158 mounted to the inner collar 148. The second carriage 158 couples to the second guide 114. Accordingly, rotation of the inner collar 148 rotates the second carriage 158 which rotates the second guide 114. Likewise, translation of the inner collar 148 translates the second carriage 158 which translates the second guide 114 along the longitudinal axis LA. The second carriage 158 is generally disposed within the first carriage 156 (e.g., the radially inward of the first carriage).

Figure 16:
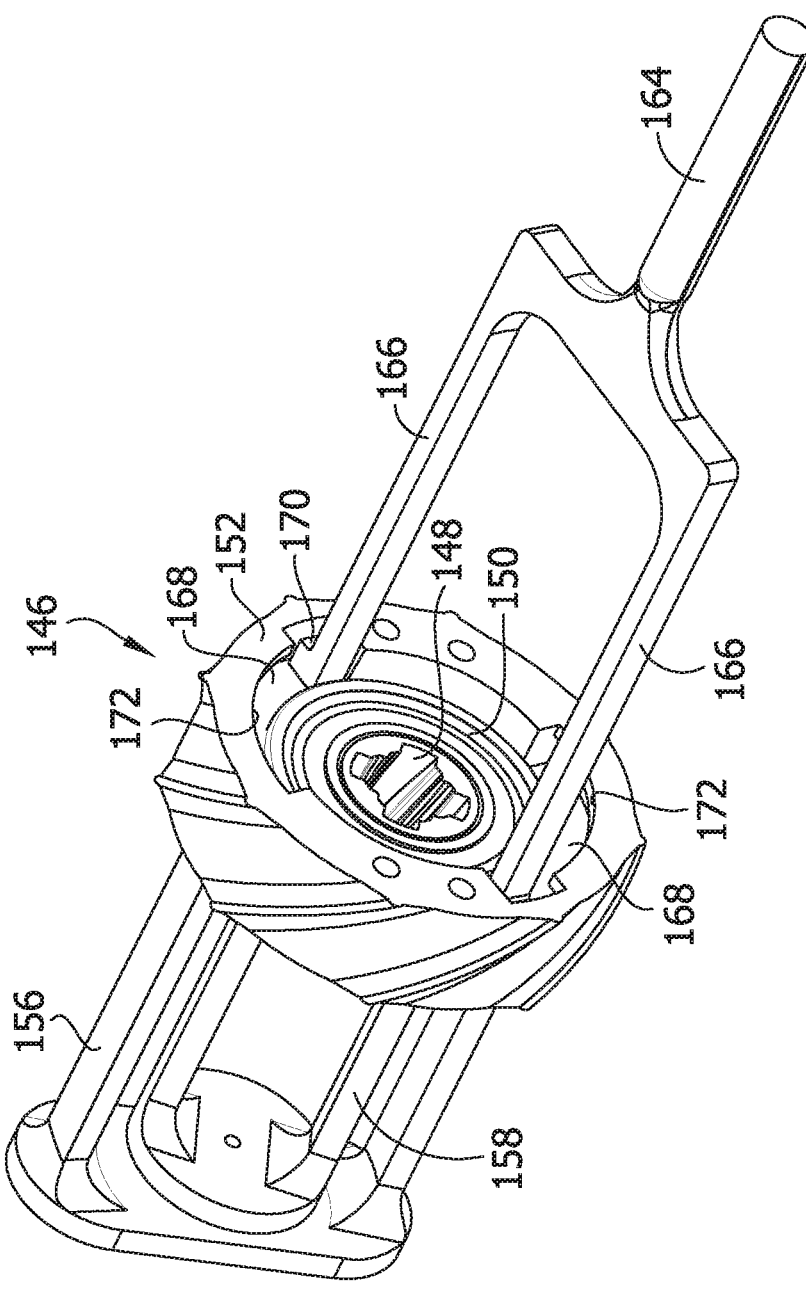
FIG. 16 is a rear perspective of a plunger of the drive assembly in an insertion position.
Figure 17:
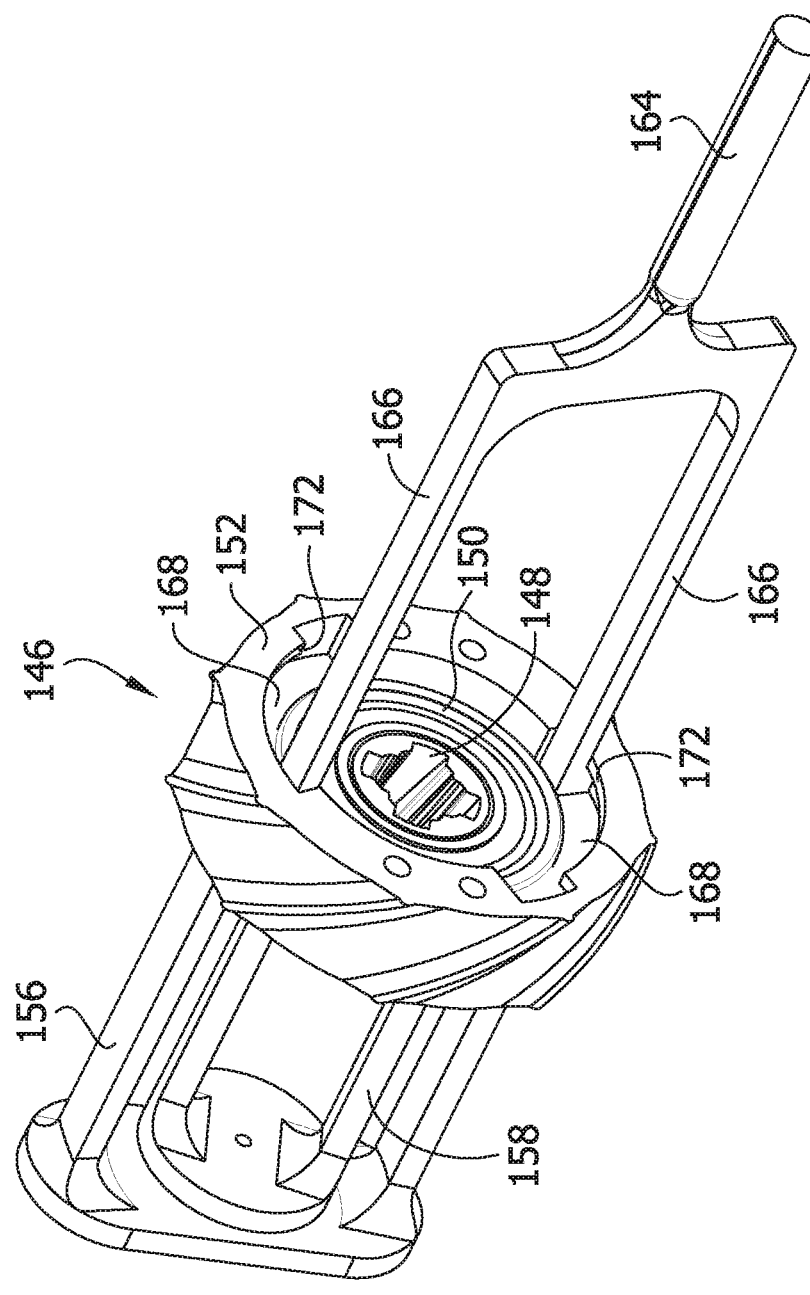
FIG. 17 is a rear perspective of the plunger in a withdrawal position.
Figure 18:
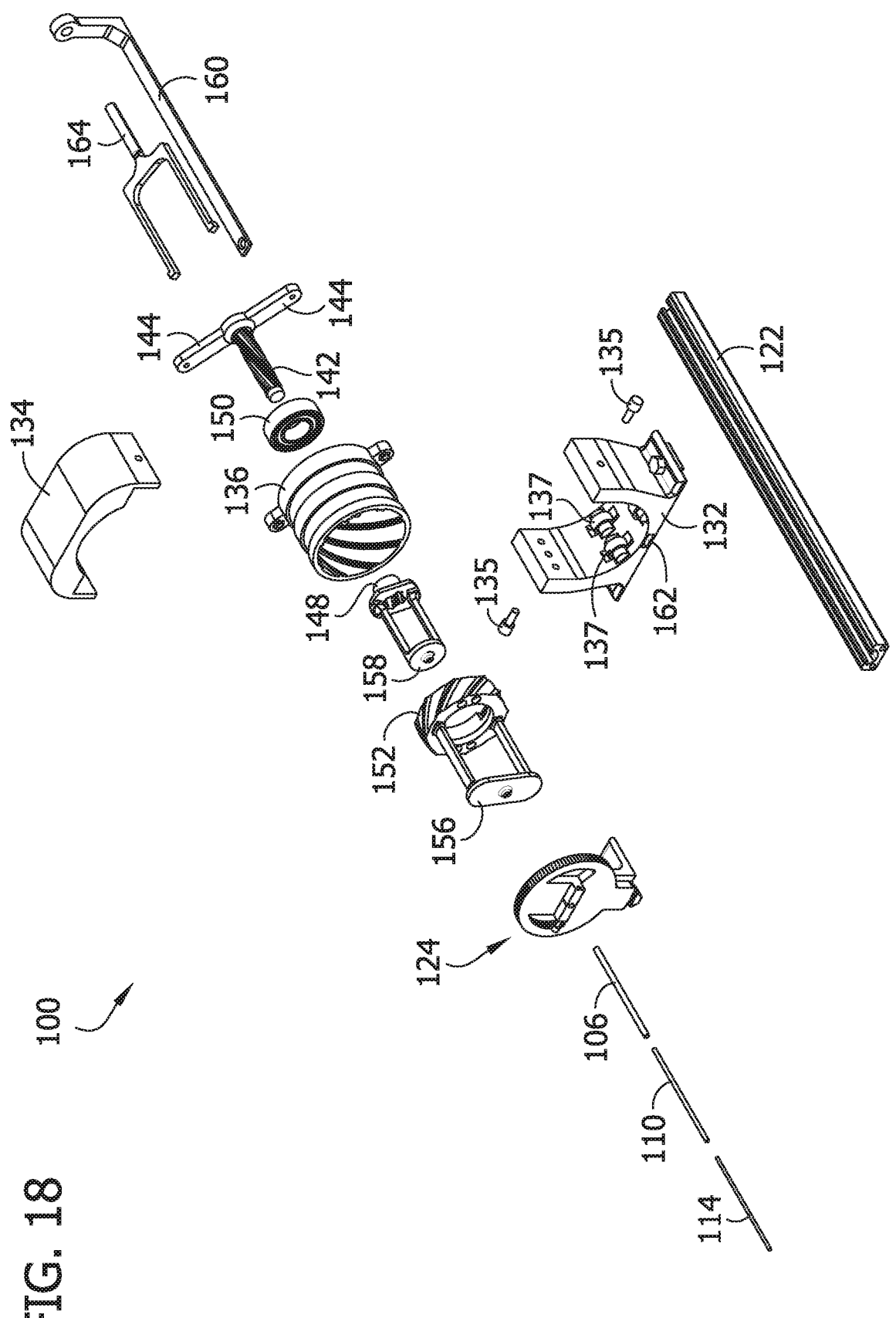
FIG. 18 is an exploded view of the delivery system.

The drive assembly 120 includes a push bar 160 (broadly, an actuator) to drive longitudinal movement of the tool sheath 106, and the first and second guides 110, 114 and the rotational movement of the first and second guides. In this embodiment, the longitudinal movement of the delivery sleeve 102 is done separately, such as by manually moving the delivery sleeve mount (broadly, an actuator) along the track 122. The push bar 160 is operatively coupled to the tool sheath mount 124 and the rotation drive assembly 146. In the illustrated embodiment, the push bar 160 extends through a slot 162 in the lower housing 132 and is coupled to the tool sheath mount 124 via the first retainer 126. The first retainer 126 permits the push bar 160 to be selectively attached and detached from the tool sheath mount 124. The push bar 160 is free to slide within the slot 162 (e.g., movement of the push bar does not move the lower housing 132). The push bar 160 includes an aperture generally aligned with the longitudinal axis LA. The drive assembly 120 includes a plunger 164 that extends through the aperture. In this manner, the plunger 164 is rotatable relative to the push bar 160. The plunger 164 operatively connects the push bar 160 with the rotation drive assembly 146. The plunger 164 includes first and second legs 166 which extend to and engage the rotation drive assembly 146 (specifically, the outer collar 152). In the illustrated embodiment, the outer collar 152 includes channels or grooves 168 that receive the ends of the legs 166 (FIGS. 16 and 17). The ends of the legs 166 may include an outstanding flange 170 or catch configured to engage a lip 172 of the outer collar 152. This engagement allows the rotation drive assembly 146 to be moved proximally along the longitudinal axis LA, as discussed in more detail below. The plunger 164 may be releasably coupled to the rotation drive assembly 146. For example, in an insertion position (FIG. 16) the plunger 164 can move proximally away from the rotation drive assembly 146. The insertion position also allows the plunger 164 to be inserted into the channels 168 of the rotation drive assembly 146. However, in a withdrawal position (FIG. 17), the plunger 164 is coupled to the rotation drive assembly 146

(e.g., the outstanding flanges 170 engage the lips 172) such that moving the plunger 164 proximally also moves the rotation drive assembly proximally. The plunger 164 is permitted to move freely within the channels 168 and may only rotate about the longitudinal axis LA as necessary (e.g., when contacted by one of the ends of the channels).

Having an independent mount 124 for the tool sheath 106 ensures that the tool sheath will move in tandem with the first and second guides 110, 114 without relying on the first and second guides to generate the forces needed to deploy it. In essence, it prevents a "dragging" behavior as the tool sheath 106 is delivered. Other configurations of the drive system 120 are within the scope of the present disclosure.

In one embodiment, the delivery system 100 may include several different sets (e.g., pairs) of first and second guides 110, 114, each set having a different pre-curved configuration. In this manner, the delivery system 100 may be a kit-of-parts with the surgeon selecting the guide or guides 110, 114 necessary to reach the desired target location in the surgical site S. In other words, the surgeon selects the first and/or second guides 110, 114 based of their curvature and the curvature needed to reach the target location at the surgical site S. In one embodiment, the delivery system 100 may include three different sets of first and second guides 110, 114, each set having a different curvature.

Figure 4:
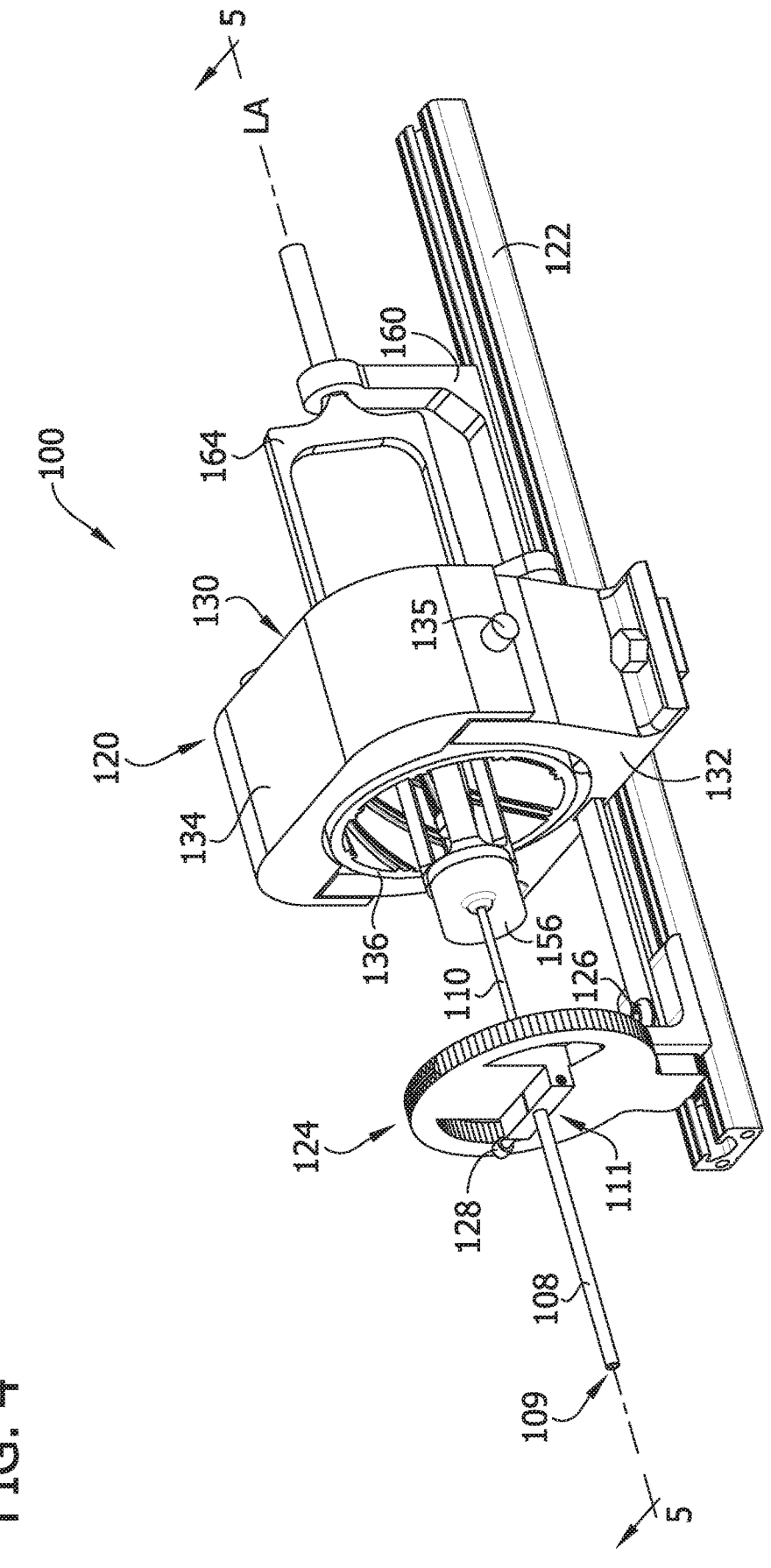
FIG. 4 is a front perspective of a delivery system according to one embodiment of the present disclosure, the delivery system in a start position.
Figure 5:
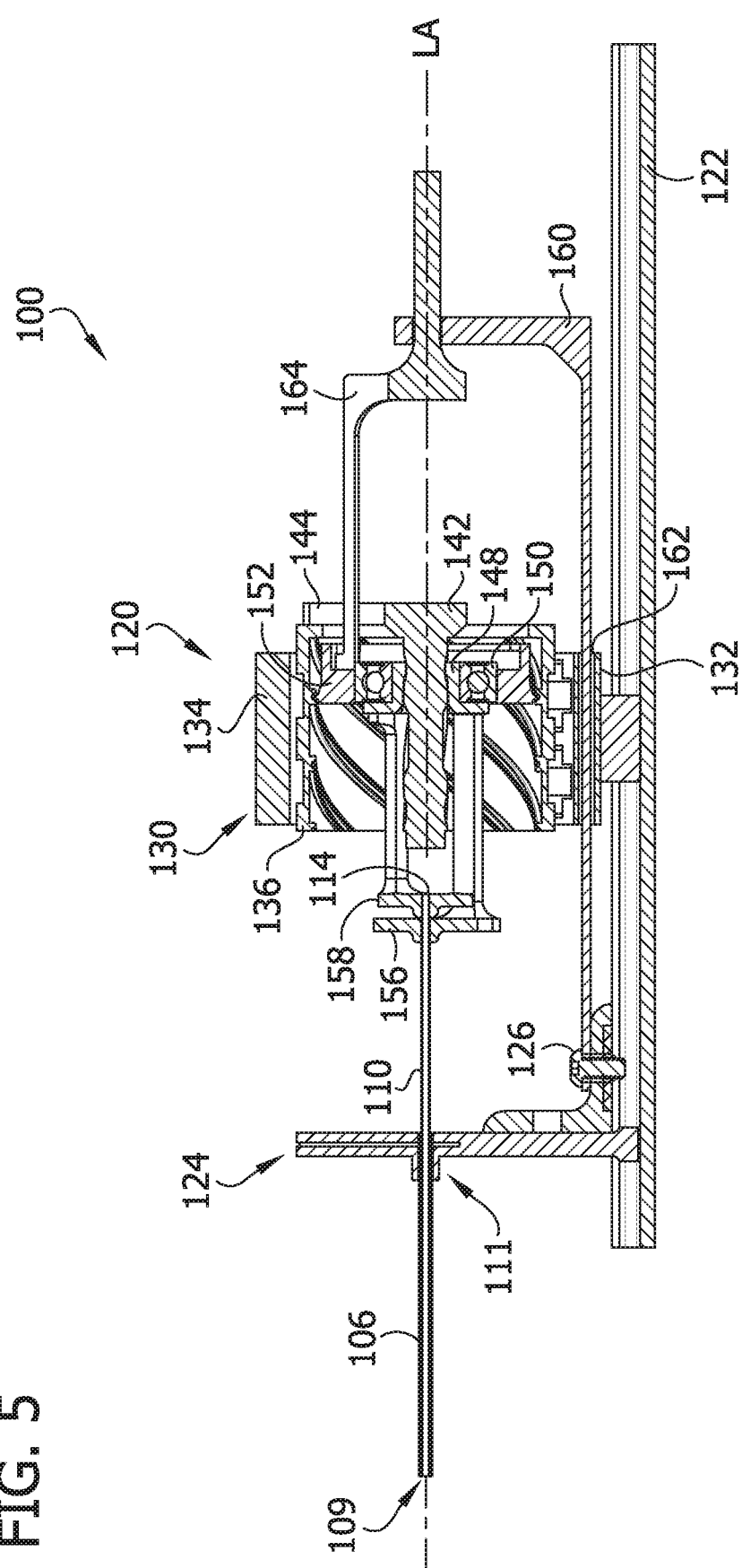
FIG. 5 is a cross-section of the delivery system taken through line 5-5 of FIG. 4.
Figure 12A:
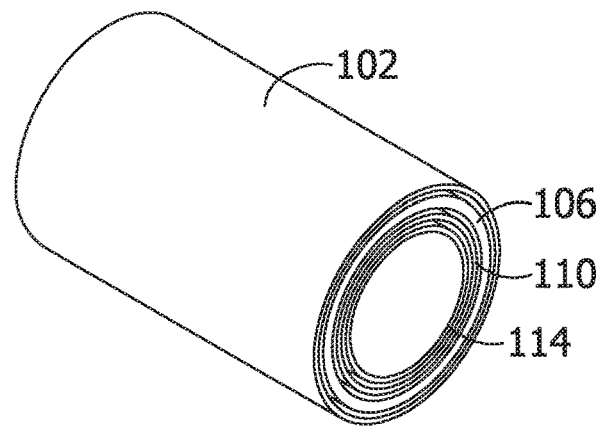
FIGS. 12A-12C are fragmentary perspectives of the delivery sleeve, the tool sheath, the first guide and the second guide illustrating the longitudinal movement of these components relative to one another.

The operation of the delivery system 100 with drive system 120 will now be described. In operation, the straight trajectory surgical tool is removed after it has been used to treat as much of the surgical site S as possible. Next, the delivery system 100 is positioned. The delivery sleeve 102, the tool sheath 106 and the first and second guides 110, 114 are positioned in the subject's body (e.g., the brain B) according to the depth of the surgical site S, using the same opening used by the straight line surgical tool. This is done by moving the delivery sleeve mount, the tool sheath mount 124 and the guide mount 130 along the track 122. This positioning results in the distal end 109 of the tool sheath 106 being spaced apart from the final location within the surgical site S desired to be reached. This distance will be traversed by the translational movement of the tool sheath 106 described below. In this initial or start positioning (FIGS. 4 and 5), the first and second guides 110, 114 are in the first configuration, such that they are generally straight (e.g., the longitudinal axis LA is straight) (FIGS. 4 and 5). With the delivery system 100 in the start position, the tool sheath 106 is ready to be advanced to the target location at the surgical site S (FIG. 12A). Before the delivery system 100 is moved to this start position, the surgeon may rotate and set the guide collar 136 and guide shaft 142 relative to the lower and upper housings 132, 134 using the openings 140 to set the direction of curvature imparted by the first and second guides 110, 114.

Figure 6:
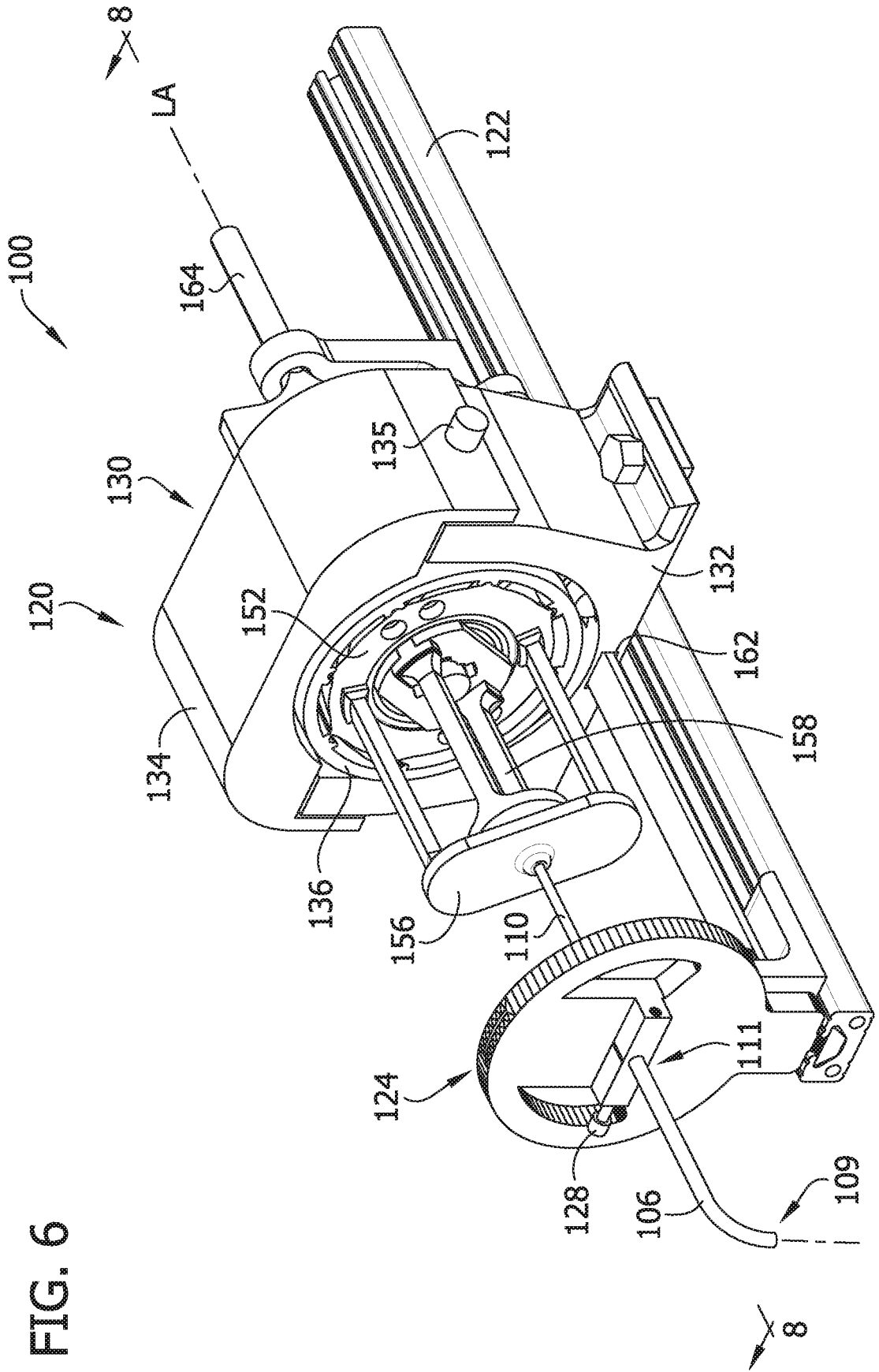
FIG. 6 is a front perspective of the delivery system in an end position.
Figure 7:
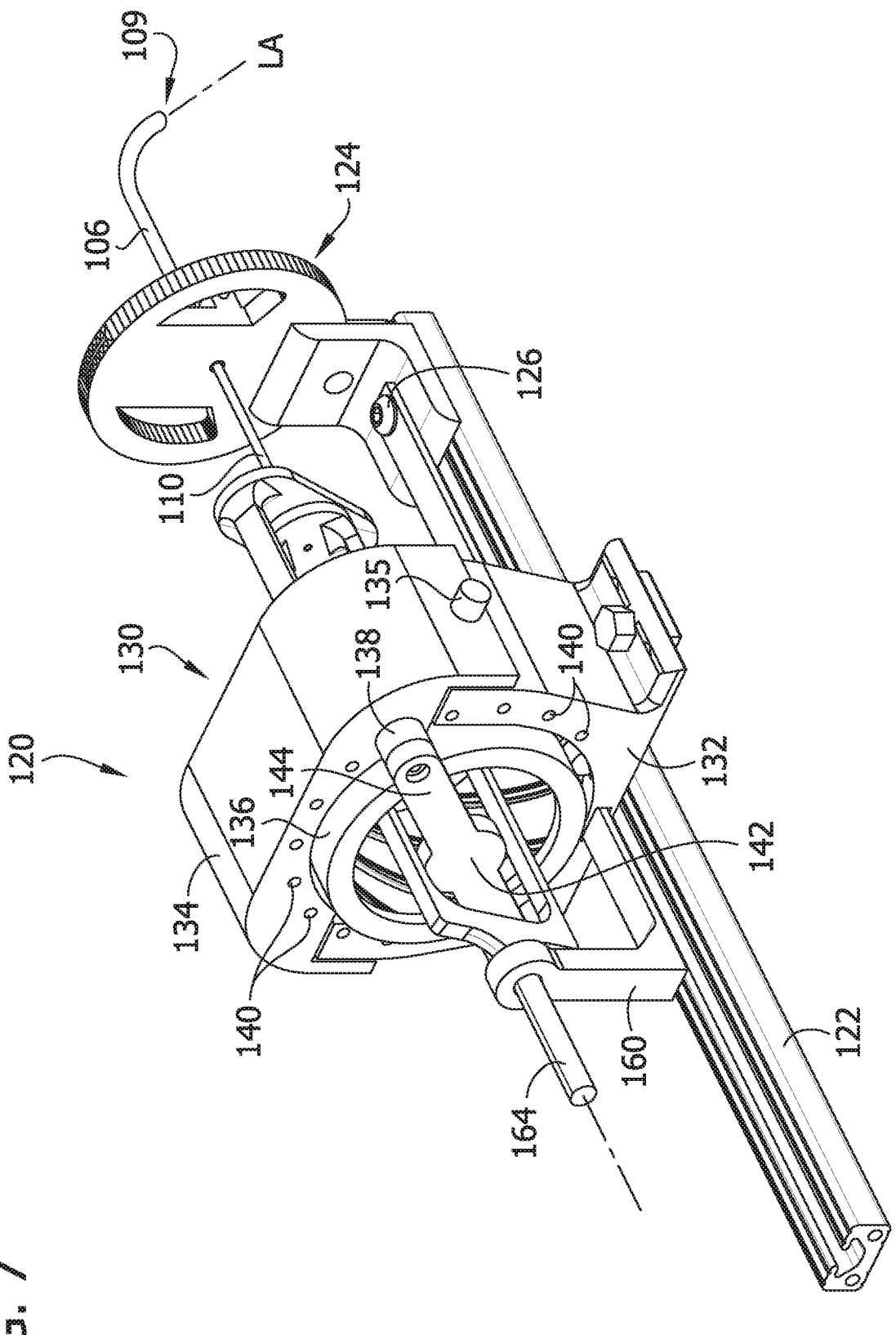
FIG. 7 is a rear perspective of the delivery system in the end position.
Figure 8:
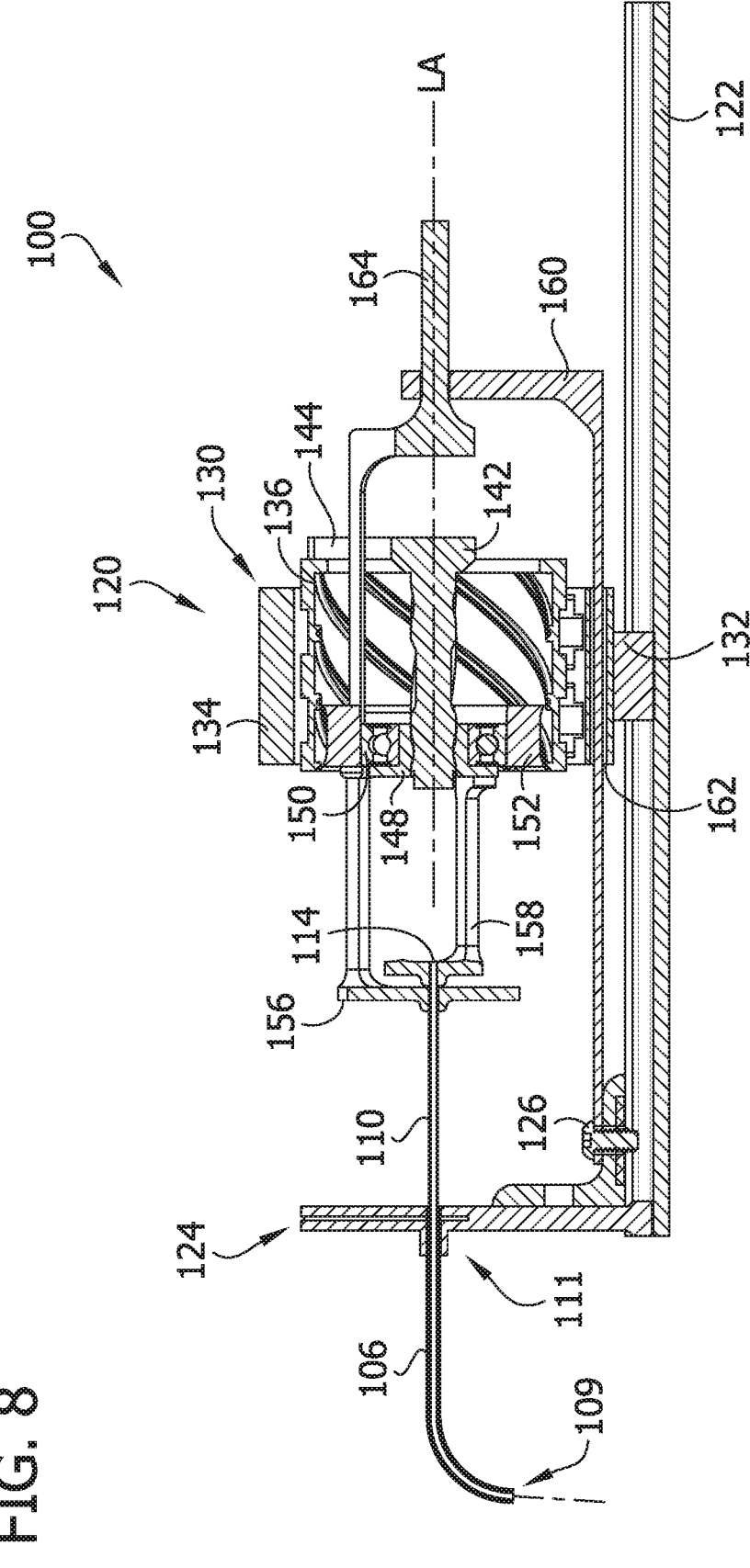
FIG. 8 is a cross-section of the delivery system taken through line 8-8 of FIG. 6.
Figure 12B:
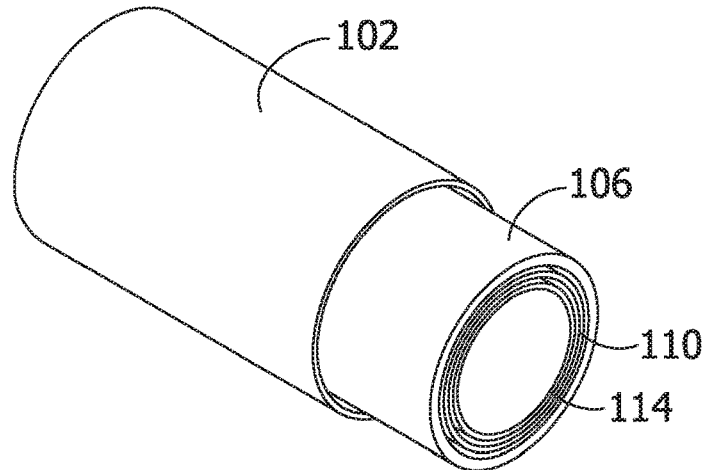

To advance the tool sheath 106 to the target location at the surgical site S, the delivery system 100 is moved to an end position (FIGS. 6-8). Specifically, the surgeon engages the push bar 160 and moves the push bar distally. As the push bar 160 is moved distally, the push bar moves the tool sheath mount 124 distally, thereby moving the tool sheath 106 toward the target location at the surgical site S (FIG. 12B). At the same time, the push bar 160 pushes the plunger 164 distally. This moves the first and second guides 110, 114 distally and rotates the first and second guides relative to one another, simultaneously, and with the distal movement of the tool sheath 106. As the push bar 160 pushes the plunger 164 distally, the plunger pushes the rotation drive assembly 146 distally along the guide collar 136 and guide shaft 142. The guide collar 136, guide shaft 142, and lower and upper housings 132, 134 are fixed in position on the track 122 and do not move with the push bar 160. As the plunger 164 pushes the rotation drive assembly 146 distally, the first and second guides 110, 114 move distally along the longitudinal axis LA (FIG. 12B) and rotate about the longitudinal axis LA simultaneously. As the outer collar 152 moves distally, the exterior threads of the outer collar engage the internal threads of the guide collar 136, thereby causing the outer collar to rotate in one direction. Likewise, as the inner collar 148 moves distally, the interior thread of the inner collar engage the external thread of the guide shaft 142, thereby causing the inner collar to rotate in the other direction. In one embodiment, the inner and outer collars 148, 152 (e.g., first and second guides 110, 114) each rotate about 90 degrees (in opposite directions) about the longitudinal axis LA as the rotation drive assembly 146 is moved from the start position to the end position. This results in the first and second guides 110, 114 rotating about 180 degrees relative to one another such that in the end position, the first and second guides are positioned to have the maximum degree of curvature in the second configuration. As the first and second guides 110, 114 rotate relative to one another (and as they are advanced distally), the first and second guides 110, 114 begin to curve (e.g., return to their natural pre-curved state), thereby curving the tool sheath 106 (e.g., the longitudinal axis LA). This creates a curved trajectory that the tool sheath 106 and first and second guides 110, 114 continue to follow until they reach the end position. Accordingly, as the first and second guides 110, 114 move longitudinally along the longitudinal axis LA, the first and second guides curve toward the desired location at the surgical site S, thereby guiding the tool sheath 106 to the desired location. In one embodiment, the distal end 109 of the tool sheath 106 is disposed at the desired location in the surgical site S when the delivery system 100 is in the end position. In another embodiment, the tool sheath 106 and the first and second guides 110, 114 may continue to be advanced distally (along the now defined curved trajectory) to position the distal end 109 of the tool sheath at the desired location. In this embodiment, the first and second guides 110, 114 would stop rotating once they reached the end position (e.g., the guide mount 130 and tool sheath mount 124 would be advanced distally along the track 122).

Figure 9:
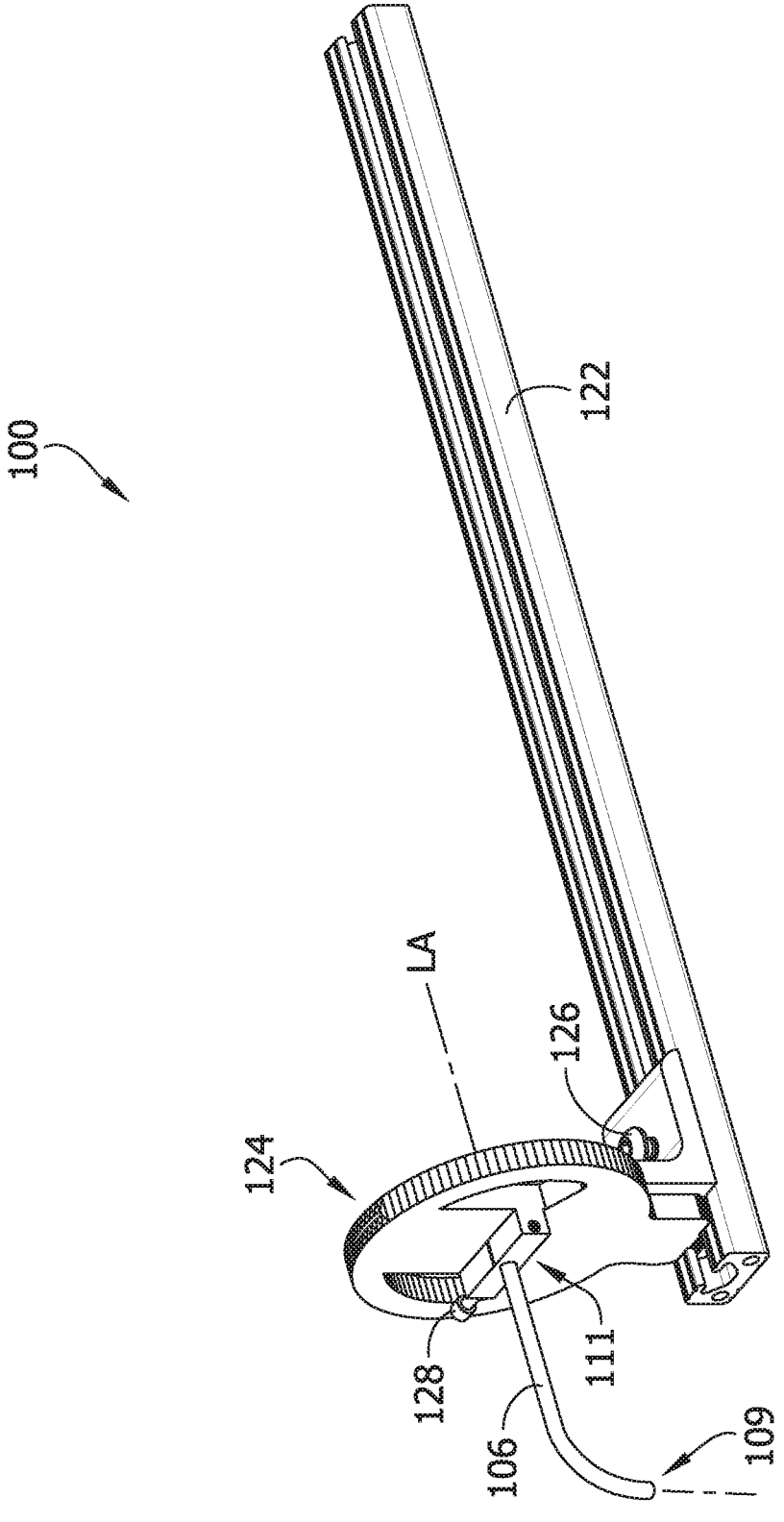
FIG. 9 is a front perspective of the delivery system with a drive assembly thereof removed.
Figure 10:
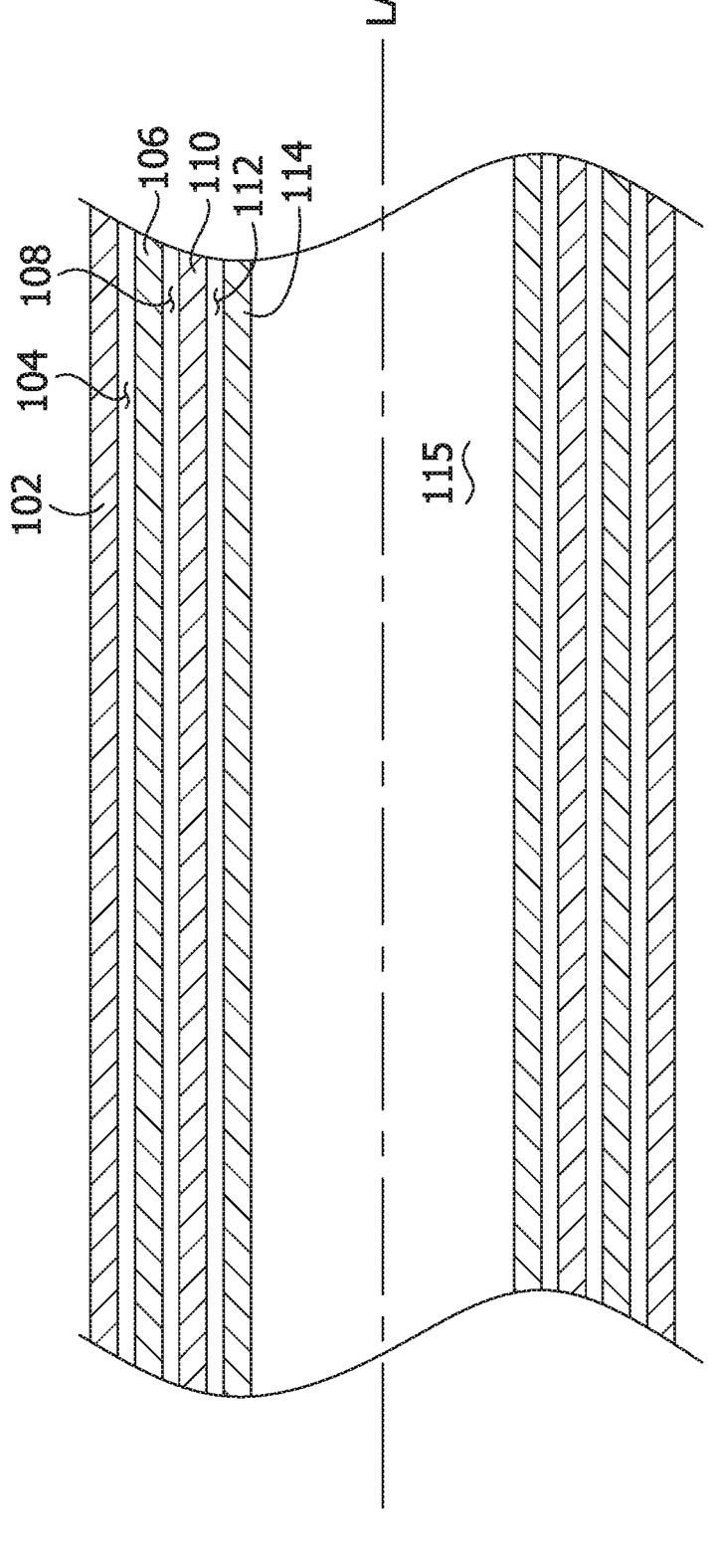
FIG. 10 is an enlarged, fragmentary cross-sectional view of a delivery sleeve, a tool sheath, a first guide and a second guide of the delivery system.
Figure 11:
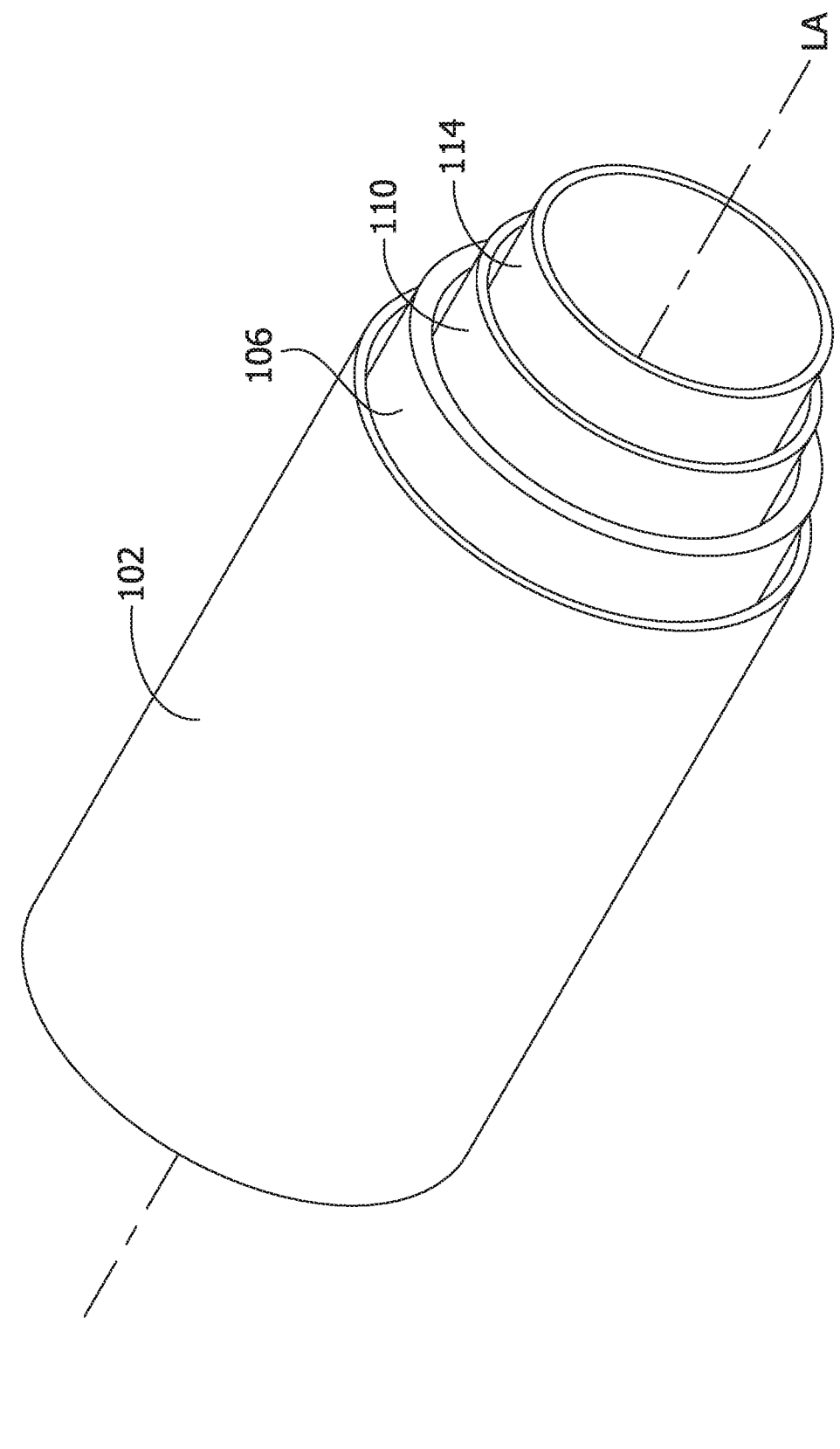
FIG. 11 is a fragmentary perspective of the delivery sleeve, the tool sheath, the first guide and the second guide.
Figure 12C:
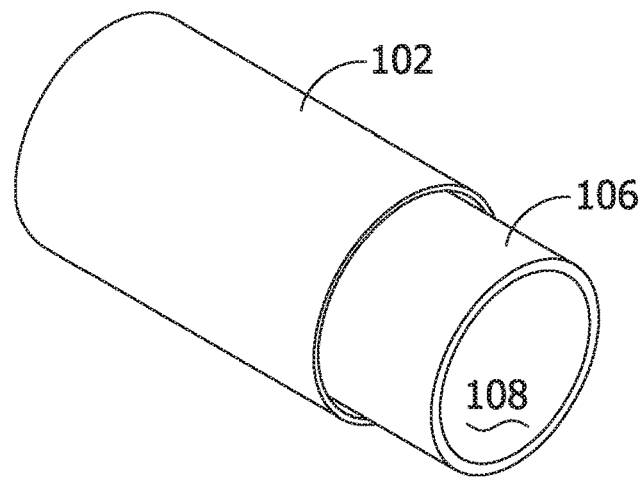

Once the distal end 109 of the tool sheath 106 is positioned in the surgical site S, the tool sheath 106 is secured in place on the track 122. The surgeon uses the first retainer 126 to disconnect the push bar 160 from the tool sheath mount 124 and secure the tool sheath mount in position on the tract 122. The surgeon then places the plunger 164 in a withdrawal position (FIG. 17) such that the outstanding flanges 170 engage the lips 172 of the rotation drive assembly 146. In this position, moving the plunger 164 proximally, moves the rotation drive assembly 146 proximally. As the rotation drive assembly 146 moves proximally, the inner and outer collars 148, 152 (e.g., the first and second guides 110, 114) rotate back toward the first configuration. This allows the first and second guides 110, 114 to withdraw from the tool sheath 106 without affecting the curved shape the first and second guides imparted on the tool sheath. Once in the start position, the guide mount 130 may be removed from the track 122 to remove the first and second guides 110, 114, thereby leaving the tool sheath 106 at the surgical site S (FIGS. 9 and 12C). At this point, a surgical tool T may be inserted through the tool sheath 106 to treat the formerly out of reach locations within the surgical site S (FIG. 19) (e.g., reach off-axis targets).

To retract the tool sheath 106 after the treatment, the first and second guides 110, 114 are inserted back into the tool sheath in the same manner described above in relation to positioning the tool sheath. Once at the end position, the push bar 160 is then reconnected to the tool sheath mount 124. The plunger 164 is moved proximally to withdrawn the tool sheath 106 and first and second guides 110, 114 back to the start position. Again in this position, the longitudinal axis LA is generally straight. This allows the tool sheath 106 to be withdrawn from the surgical site S along the same trajectory the tool sheath was moved toward the surgical site, minimizing any damage to the surrounding tissue. Once back the start position, the entire delivery system 100 may then be removed from the subject. At this point, a surgeon can change the direction of curvature by rotating the guide shaft 142 and guide collar 136 relative to the lower and upper housings 132, 134 and setting the new orientation using the holes 140 to restart the process again and direct the tool sheath to a different target location within the surgical site S. For example, by repeating this process, the surgeon can reach different locations L1, L2, L3 (L2 and L3 are shown in dashed lines in FIG. 19) within a surgical site S.

Generally speaking, one embodiment of a method for accessing a surgical site S (e.g., a location with a subject's brain B) includes advancing a distal end of the delivery system, as described herein (i.e., delivery system 100) through the body tissue of a subject to position the distal end of the delivery system in the body tissue and a proximal end of the delivery system outside the body tissue. The delivery system 100 guides a surgical tool T to the surgical site S. The method includes guiding the distal end of the delivery system 100 to the surgical site S by longitudinally moving the first guide 110 and the tool sheath 106 relative to the delivery sleeve 102. The method further includes retracting the first guide 110 proximally through the tool sheath 106 such that the distal end of the delivery system 100 is defined by the distal end 109 of the tool sheath 106.

Moving the first guide 110 relative to the delivery sleeve 102 may move the distal end of the delivery system 100 out of alignment with the straight longitudinal axis LA (e.g., off axis). This allows the distal end of the delivery system 100 to be positioned closer to a desired location within the surgical site S. In one embodiment, the first guide 110 is moved distally relative to the delivery sleeve 102. The first guide 110 is deformable and has a generally curved shape in its undeformed state. At least a portion of the first guide 110 is curved when the first guide is moved distally relative to the delivery sleeve 102. In particular, the portion of the first guide 110 distal of the delivery sleeve 102 is no longer constrained (e.g., deformed) by the delivery sleeve and returns to its curved or undeformed state. In one embodiment, the first guide 110 and the tool sheath 106 are moved together.

The method may further include removing the first guide 110 from the tool sheath 106. In other words, the method may further include removing any components containing Nitinol or other imaging interfering materials from the distal end of the delivery system 110. The method may also include advancing a surgical tool T distally though the tool sheath 106 to position the surgical tool at the desired location at the surgical site S. The method may also include imaging the surgical site S to determine the position of the distal end 109 of the tool sheath 106 relative to the surgical site after the first guide 110 has been retracted. As a result of removing the first guide 110 from the tool sheath 106, any images taken of the surgical site S during the surgical procedure showing the position of the surgical tool T relative to the surgical site are clear and unobstructed by the delivery system 100 (specifically the tool sheath).

The method may include using a delivery system 100 having a second guide 114 movably disposed longitudinally within the first guide 110 such that guiding the distal end of the delivery system to the surgical site S includes longitudinally moving the first and second guides relative to the delivery sleeve 102. The first and second guides 110, 114 may be moved together relative to the delivery sleeve 102. Additionally or alternatively, the first and second guides 110, 114 may be moved longitudinally relative to one another. Additionally or alternatively, the first and second guides 110, 114 may be rotated relative to one another when guiding the distal end of the delivery system 100. Accordingly, due to the curves of the first and second guides 110, 114 and the ability to position the curves of the first and second guides relative to one another, as described herein, moving the first and second guides together relative to the delivery sleeve 102 either moves the distal end of the delivery system 100 out of alignment with the longitudinal axis LA or moves the distal end of the delivery system along the longitudinal axis.

An important component of the above delivery system 100 is the tool sheath 106. The tool sheath 106 must be flexible enough to be shaped by and follow the first and second guides 110, 114, but rigid enough to maintain its shape when sitting in brain tissue once the first and second guides are removed. For example, the tool sheath 106 may behaving similar to a flexible straw embedded in gelatin. Because of the flexibility and cushion of the surrounding environment, the tool sheath 106 placement and configuration by the first and/or second guides 110, 114 and the maintaining of the tool sheath placement and configuration after the first and second guides are retracted is achieved.

Other embodiments of the delivery system are within the scope of the present disclosure. For example, in one alternative embodiment, a delivery system (not shown) may not include the delivery sleeve 102 and the tool sheath 106 but otherwise is generally similar to delivery system 100. In this embodiment, the delivery system includes the first and second guides 110, 114, with the second guide 114 defining a second guide lumen 115 (FIG. 10) sized and shaped to receive the surgical tool T. In other words, in this embodiment, the first and second guides 110, 114 form the tool sheath which guides the surgical tool T to the desired location at the surgical site S. In this embodiment, the first and second guides 110, 114 are preferably made out of a material that does not interfere with the imaging of the surgical site S but still has the super elasticity required to form the different trajectories (e.g., curved and straight). This way, the first and second guides 110, 114 can remain at the surgical site S and guide the surgical tool T to the desired location while not interfering with the imaging of the surgical site. For example, the first and second guides 110, 114 can be made of one or more polymers that do not interfere with the imaging of the surgical site S but still provide the necessary elasticity. For example, polymers include polyamides, such as synthetic polyamides (e.g., various nylons including nylon 6,6 and nylon 6), polyvinyl chloride (PVC), polycaprolactone (PCL), polydioxanone (PDO), or a fluoropolymer. Fluoropolymers include, for example, polytetrafluoroethylene (PTFE), fluorinated ethylene-propylene (FEP), perfluoroalkoxy resin (PFE, a copolymer of tetrafluoroethylene and perfluorovinylethers), ethylene-tetrafluoroethylene copolymer (ETFE), polychlorotrifluoroethylene (PCTFE), ethylene-chloro-trifluoroethylene copolymer (ECTFE), polyvinylidene fluoride (PVDF), and polyvinyl fluoride (PVF). Preferably the fluoropolymer is PTFE. In one embodiment, the first and second guides 110, 114 are formed by electrospinning the biocompatible polymer. Otherwise, the first and second guides 110, 114 are generally the same as described above (hence the same reference numbers) and operate in the same way.

In this embodiment, the delivery system without the delivery sleeve and tool sheath may also include any drive system described herein, such as drive system 120. In this case the drive system would still include the guide mount 130 and the plunger 164 (and possibly the push rod 160), which are generally need to translate and rotate the first and second guides 110, 114 relative to the longitudinal axis LA. However, the drive system would not include the delivery sleeve mount and the tool sheath mount. In addition, the drive system may include first and second guide mounts (not shown) to secure the first and second guides 110, 114 in position. The first and second guide mounts may be generally the same as the tool sheath mount 124 described above. The first and second guide mounts would secure the first and second guides 110, 114 in position, when the first and second guides are in the end position and/or second configuration, to allow the guide mount 130 to be disconnected from the first and second guides to permit the surgical tool T to be entered into the second guide lumen 115. Other configurations are within the scope of the present disclosure.

This embodiment of the delivery system would operate in a similar manner to delivery system 100 except without the delivery sleeve and tool sheath. For example, in general, one method for accessing the surgical site S using this delivery system includes advancing a distal end of the delivery system through the body tissue of a subject to position the distal end of the delivery system in the body tissue and a proximal end of the delivery system outside the body tissue. In this embodiment, the distal end of the delivery system is defined by the distal end of the second guide 114 and/or first guide 110. The method includes guiding the distal end of the first and/or second guide 110, 114 to the surgical site S by longitudinally moving the first and second guides 110, 114 along the longitudinal axis LA and rotating the first and second guides about the longitudinal axis. Rotating the first and second guides 110, 114 relative to one another moves the distal end of the first and/or second guide out of alignment with the straight longitudinal axis LA (as described above). In other words, as described above, rotating the first and second guides 110, 114 relative to one another creates the curved trajectory used to guide the first and second guides to the desired location at the surgical site S. Due to the curves of the first and second guides 110, 114 and the ability to position the curves of the first and second guides relative to one another, as described herein, rotating the first and second guides together relative to one another can result in the longitudinal axis LA having a first shape (e.g., straight shape) with the guides in the first configuration and a different second shape (e.g., curved shape) with the guides in the second configuration. The method further includes inserting a surgical tool T through the lumen 115 of the second guide 114 to apply treatment at the surgical site, after the first and second guides 110, 114 have been positioned. The method may further include imaging the surgical site S to ensure the surgical tool T is properly positioned. The method may further include retracting the first and second guides 110, 114 from the surgical site S after the treatment is completed with the surgical tool T (and the surgical tool is withdrawn). Withdrawing the first and second guides 110, 114 may include moving the guides proximally while the guides rotate back to their start positions (e.g., rotate back to a straight line trajectory), for reasons described herein. This process can then be repeated for different locations within the surgical site S by resetting the direction of curvature of the first and second guides 110, 114 as described herein.

Embodiments of a method of performing a surgical procedure in a subject's brain comprise accessing the surgical site within the subject's brain according any of the methods described herein; advancing a surgical tool distally though the tool sheath to position the surgical tool at the surgical site; and operating the surgical tool. In various embodiments, the surgical tool comprises an ablation tool such as a laser ablation tool (e.g., a laser ablation tool suitable for LITT).

The methods of the present disclosure can be used for a wide range of subjects. In various embodiments, the subject is a mammal (e.g., a human).

The delivery systems and methods described herein are suitable to serve as a "touch-up" procedure for existing procedures using straight trajectories initially to treat the majority of the surgical site S. When the curved path is needed, the surgeon uses the delivery systems described herein with the existing straight yet flexible surgical tools T to steer to desired off-axis locations. However, it is understood the delivery system and methods described herein may also be used as the main procedure (e.g., straight line procedure) as well.

EXAMPLE

The following is a non-limiting example to further illustrate the present disclosure.

In one experiment, four mock tumors were placed in 12 off-axis locations within a 10% by weight Knox-Gelatin phantom tissue model. The tumors were placed at 4 cm, 6 cm, and 8 cm in depth from the entry point of the delivery system. For each tumor, the delivery system according to the present disclosure was used. The PTFE port was deployed, the cannula system was retracted, and an existing LITT probe was delivered through the port to a targeted tumor. Of the 12 tumors tested, the port was delivered deployed successfully 12 times, the cannula system was retracted successfully 11 times, and the LITT probe was delivered through the port successfully 10 times. While these results are qualitative, they illustrate the feasibility of the delivery system.

Having described the disclosure in detail, it will be apparent that modifications and variations are possible without departing from the scope of the disclosure defined in the appended claims. For example, where specific dimensions are given, it is understood these dimensions are exemplary and other dimensions are possible.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above systems and methods without departing from the scope of the disclosure, it is intended that all matter contained in the above description and shown in the accompanying drawings shall be interpreted as illustrative and not in a limiting sense.

The invention claimed is:

1. A delivery system for guiding a surgical tool to a surgical site, the delivery system comprising:

a delivery sleeve having a longitudinal axis and proximal and distal ends spaced apart from one another along the longitudinal axis, the delivery sleeve configured to be inserted into the body tissue of a subject;

a tool sheath movably disposed longitudinally within the delivery sleeve, the tool sheath defining a lumen configured to receive the surgical tool; and a first guide movably disposed longitudinally in the lumen of the tool sheath, the first guide being deformable and having a generally curved shape when the first guide is not deformed;

wherein the first guide and tool sheath are configured to be moved distal of the delivery sleeve so that the first guide can guide a distal end of the tool sheath to the surgical site;

wherein the first guide is deformed when the first guide is disposed within the delivery sleeve and at least a portion of the first guide has a generally curved shape when the first guide is moved distally through the distal end of the delivery sleeve;

wherein the tool sheath is flexible and generally conforms to the shape of the first guide; and wherein the delivery sleeve is rigid relative to the tool sheath and the first guide such that the tool sheath and the first guide conform to the shape of the delivery sleeve.

2. The delivery system of claim 1, further comprising a second guide movably disposed longitudinally within the first guide, the second guide being deformable and having a generally curved shape when the second guide is not deformed;

wherein the first and second guides and tool sheath are configured to be moved distal of the delivery sleeve so that the first and second guides can guide the distal end of the tool sheath to the surgical site;

wherein the second guide is deformed when the second guide is disposed within the delivery sleeve;

wherein the first and second guides are configured to move at least one of longitudinally and rotationally relative to one another to change the relative shapes of the first and second guides; and wherein the tool sheath generally conforms to the shapes of the first and second guides.

3. The delivery system of claim 1, wherein the first guide is configured to be removed from the lumen of the tool sheath to permit the surgical tool to be inserted into the lumen.

4. The delivery system of claim 1, further comprising a drive assembly operatively connected to the delivery sleeve, the tool sheath and the first guide and configured to move the delivery sleeve, the tool sheath and the first guide into the body tissue of the subject.

5. The delivery system of claim 4, wherein the drive assembly is configured to move the delivery sleeve, the tool sheath and the first guide together and move each of the delivery sleeve, the tool sheath and the first guide relative to one another.

6. The delivery system of claim 4, wherein the drive assembly is configured to rotate the first guide relative to the delivery sleeve and the tool sheath.

7. A delivery system for guiding a surgical tool to a surgical site, the delivery system comprising:

a first guide having a longitudinal axis and proximal and distal ends spaced apart from one another along the longitudinal axis, the first guide configured to be inserted into the body tissue of a subject, the first guide defining a lumen extending between the proximal and distal ends, the first guide being deformable and having a generally curved shape when the first guide is not deformed;

a second guide movably disposed in the lumen of the first guide, the second guide being deformable and having a generally curved shape when the second guide is not deformed; and a delivery sleeve configured to be inserted into the body tissue of a subject, the first and second guides movably disposed within the delivery sleeve, the delivery sleeve being rigid relative to the first and second guides such that the first and second guides conform to the shape of the delivery sleeve; and wherein the longitudinal axis has a first shape when the first and second guides are disposed relative to one another in a first configuration and a second shape different than the first shape when the first and second guides are disposed relative to one another in a second configuration.

8. The delivery system of claim 7, wherein the longitudinal axis is generally straight when the first and second guides are in the first configuration and wherein at least a portion of the longitudinal axis is curved when the first and second guides are in the second configuration.

9. The delivery system of claim 7, further comprising a tool sheath defining a tool sheath lumen, wherein the first and second guides are movably disposed within the tool sheath lumen, wherein the tool sheath is movably disposed within the delivery sleeve, wherein the tool sheath is flexible and generally conforms to the shape of the first and second guides and the delivery sleeve.

10. The delivery system of claim 9, wherein the tool sheath lumen is sized and shaped to receive the surgical tool.

11. The delivery system of claim 7, wherein the second guide defines a second guide lumen sized and shaped to receive the surgical tool.

12. The delivery system of claim 7, further comprising a drive assembly operatively coupled to the first and second guides and the delivery sleeve, the drive assembly configured to move the first and second guides and delivery sleeve simultaneously.

13. The delivery system of claim 12, wherein the drive assembly is configured to move the first and second guides independently of one another.

14. The delivery system of claim 12, wherein the drive assembly is configured to move the first and second guides along the longitudinal axis.

15. The delivery system of claim 12, wherein the drive assembly is configured to rotate the first and second guides about the longitudinal axis.

16. The delivery system of claim 2, wherein the first and second guides each comprises a nickel-titanium shape memory alloy.

17. The delivery system of claim 16, wherein the tool sheath is a constructed of a polymer.

18. The delivery system of claim 7, wherein the first and second guides each comprises a nickel-titanium shape memory alloy.

19. The delivery system of claim 7, further comprising a tool sheath defining a lumen, the first and second guides being disposed in the lumen of the tool sheath.

20. The delivery system of claim 19, further comprising a drive assembly operatively coupled to the first and second guides, the drive assembly configured to rotate the first and second guides relative to one another and relative to the tool sheath.

\* \* \* \* \*